US007223388B2

(12) United States Patent
Tarrand et al.

(10) Patent No.: US 7,223,388 B2
(45) Date of Patent: May 29, 2007

(54) MODIFIED REOVIRAL THERAPY

(75) Inventors: Jeffrey Tarrand, Houston, TX (US);
Xiang-Yang Han, Bellaire, TX (US)

(73) Assignee: Board of Regents, The Univeristy of Texas System, Austin, TX (US)

( * ) Notice: Subject to any disclaimer, the term of this patent is extended or adjusted under 35 U.S.C. 154(b) by 451 days.

(21) Appl. No.: 10/211,218

(22) Filed: Aug. 2, 2002

(65) Prior Publication Data
US 2003/0039656 A1 Feb. 27, 2003

Related U.S. Application Data

(60) Provisional application No. 60/310,206, filed on Aug. 3, 2001.

(51) Int. Cl.
A61K 39/15 (2006.01)
A61K 48/00 (2006.01)
A61K 47/00 (2006.01)
A61K 47/02 (2006.01)
A61K 39/00 (2006.01)
A61B 5/055 (2006.01)

(52) U.S. Cl. .................. 424/93.1; 424/490; 424/215.1; 424/141.1; 424/9.43; 424/9.322; 424/9.411

(58) Field of Classification Search ................ 432/93.1; 424/215.1, 155.1, 497, 93.1, 205.1, 9.431, 424/9.411, 490; 435/320.1
See application file for complete search history.

(56) References Cited

U.S. PATENT DOCUMENTS

| 5,192,540 | A | 3/1993 | Kuo et al. |
| 5,658,779 | A | 8/1997 | Krupey et al. |
| 6,110,461 | A | 8/2000 | Lee et al. |
| 6,136,307 | A | 10/2000 | Lee et al. |
| 6,267,987 | B1 * | 7/2001 | Park et al. ................... 424/486 |
| 6,455,038 | B1 | 9/2002 | Lee et al. |
| 6,565,831 | B1 * | 5/2003 | Coffey et al. .............. 424/1.33 |
| 6,569,426 | B2 | 5/2003 | Smith et al. |

FOREIGN PATENT DOCUMENTS

| WO | WO9844143 A1 * | 10/1998 |
| WO | 00/50051 A2 | 8/2000 |
| WO | 00/50051 A3- | 8/2000 |

OTHER PUBLICATIONS

Haisma et al. Tumor-specific gene trnasfer via an adenoviral vector targeted to the pan-carcinlma antigen EpCAM, 1999, vol. pp. 1469-1474.*
MeSH pp. 1-4.*
http:// www.Answers.com/oncarbohydrate, pp. 1-8.*
The Free Dictionary On Line for carraggeenin, xanthan gum.*
Xi. et al. Phar. Res. 1996, vol. 13, No. 12, pp. 1846-1850.*
Smith, Edward R., et al.; Oncolytic viruses as novel anticancer agents: turning one scourge against another; Exp. Opin. Invest. Drugs (2000) 9(2):311-327.
Norman, Kara L., et al.; Reovirus as a novel oncolytic agent; The Journal of Clinical Investigation, vol. 105 (8), pp. 1035-1038; Apr. 2000.
Wodarz, Dominik; Viruses as Antitumor Weapons: Defining Conditions for Tumor Remission; Cancer Research 61, pp. 3501-3507, Apr. 15, 2001.
Coffey, Matthew, et al.; Reovirus Therapy of Tumors with Activated Ras Pathway; Science, vol. 282, pp. 1332-1334, Nov. 13, 1998.
Ogris, M., et al.; PEGylated DNA/transferrin-PE1 complexes: reduced interaction with blood components, extended circulation in blood and potential for systemic gene delivery; Gene Therapy (1999) 6, 595-605.
Croyle, Maria A., et al.; Technical Report—Development of a Rapid Method for the PEGylation of Adenoviruses with Enhanced Transduction and Improved Stability under Harsh Storage Conditions; Human Gene Therapy 11:1713-1722 (Aug. 10, 2000).
O'Riordan, Catherine R., et al.; PEGylation of Adenovirus with Retention of Infectivity and Protection from Neutralizing Antibody in Vitro and in Vivo; Human Gene Therapy 10:1349-1358 (May 20, 1999).
Wen, Xiaoxia, et al.; Poly(ethylene glycol)-Conjugated Anti-EGF Receptor Antibody C225 with Radiometal Chelator Attached to the Termini of Polymer Chains; Bioconjugate Chem. 12:545-553, 2001.
Yang, Xiao-Dong, et al.; Development of ABX-EGF, a fully human anti-EGF receptor monoclonal antibody, for cancer therapy; Critial Reviews in Oncology Hematology 38:17-23, 2001.
Ruoslahti, Erkki; Fibronectin and Its Integrin Receptors in Cancer; Advances in Cancer Research 76:1-20, 1999.
Robbins, J., et al. "Haemophilus Influenzae Type b Infections", Bacterial Vaccines (1984) pp. 289-316.
March, S., et al., "A Simplified Method for Cyanogen Bromide Activation of Agarose for Affinity Chromatograph", Analytical Biochem., vol. 60 (1974) pp. 149-152.
Bethell, G., et al., "A Novel Method of Activation of Cross-Linked Agaroses with 1,1'-Carbonyldiimidazole Which Gives a Matrix for Affinity Chromatography Devoid of Additional Charged Group," The Jol. of Bio. Chem., vol. 254, No. 8, (Apr. 1979) pp. 2572-2574.

(Continued)

Primary Examiner—Bruce R. Campell
Assistant Examiner—Bao Qun Li
(74) Attorney, Agent, or Firm—Fulbright & Jaworski, LLP

(57) ABSTRACT

The present invention relates to hyperproliferative diseases. Specifically, the present invention encompasses pharmaceutical compositions comprising a modified Reoviridae virus, wherein the Reoviridae virus is conjugated to a hydroxylated hydrocarbon or a polycationic polymer to reduce the clearance of the composition and reduce the immunogenicity of the composition. Yet further, the invention relates to methods of treating a hyperproliferative disease by administering to a patient an effective amount of the modified Reoviridae virus.

8 Claims, 2 Drawing Sheets

OTHER PUBLICATIONS

Tarrand, J., et al., "Clonal Characterization of the Human IgG Antibody Repertoire to Haemophilius Infulenzae Type B Polysaccharide", The Jol. of Immun., vol. 7, vol. 143, (Apr. 1989), pp. 2519-2526.

Tomasulo, S., et al., "Trittation of Endotoxin", Biochemica Biophysica Actg. vol. 400 (1975) pp. 399-406.

Bobbitt, J., et al., "Periodate Oxidation of Carbohydrates", Adv. Carbohydr. Chem. 1956. vol. 48 No. 11 pp. 1-41. Baognol.

Anderson, P. et al., "Vaccines Consisting of Periodate-Cleaved Oligosaccharides from the Capsule of Haemophilus Influenzae Type b coupled to a Protein Carrier: Structural and Temporal Requirements for Priming in the Human Infant", Jol. of Immun. (Aug. 1986) vol. 137, No. 4., pp. 1181-1186.

Haahti, Eero, et al., "The uropygiols: identification of the unsaponifiable constituent of a diester wax from chicken preen glands", Jol. of Lipids Res., (1987) vol. 8, pp. 131-137.

Axen, R., et al., "Chemical Coupling of Peptides and Proteins to Polysaccharides by Means of Cyanogen Halides", Nature, vol. 214 (Jun. 1987), pp. 1302-1304.

* cited by examiner

MODIFIED REOVIRAL THERAPY

This application claims priority to U.S. provisional application 60/310,206, which was filed Aug. 3, 2001.

A. FIELD OF THE INVENTION

The present invention relates generally to the field of hyperproliferative disease, such as cancer. More particularly, it concerns pharmaceutical compositions comprising a modified Reoviridae virus, wherein the Reoviridae virus is conjugated to a hydroxylated hydrocarbon. Yet further, the invention relates to methods of treating a hyperproliferative disease by administering to a patient an effective amount of the modified Reoviridae virus.

B. DESCRIPTION OF RELATED ART

Normal tissue homeostasis is a highly regulated process of cell proliferation and cell death. An imbalance of either cell proliferation or cell death can develop into a cancerous state (Solyanik et al, 1995; Stokke et al., 1997; Mumby and Walter, 1991; Natoli et al., 1998; Magi-Galluzzi et al., 1998). For example, cervical, kidney, lung, pancreatic, colorectal, and brain cancer are just a few examples of the many cancers that can result (Erlandsson, 1998; Kolmel, 1998; Mangray and King, 1998; Gertig and Hunter, 1997; Mougin et al., 1998). In fact, the occurrence of cancer is so high, that over 500,000 deaths per year are attributed to cancer in the United States alone.

The maintenance of cell proliferation and cell death is at least partially regulated by proto-oncogenes. A proto-oncogene can encode proteins that induce cellular proliferation (i.e., sis, erbB, src, ras and myc), proteins that inhibit cellular proliferation (i.e., Rb, p16, p19, p21, p53, NF1 and WT1) or proteins that regulate programmed cell death (i.e., bcl-2) (Ochi et al., 1998; Johnson and Hamdy, 1998; Liebermann et al., 1998). However, genetic rearrangements or mutations to these proto-oncogenes, results in the conversion of a proto-oncogene into a potent cancer-causing oncogene. Often, a single point mutation is enough to transform a proto-oncogene into an oncogene.

Currently, there are few effective options for the treatment of many common cancer types. The course of treatment for a given individual depends on the diagnosis, the stage to which the disease has developed, and factors such as age, sex, and general health of the patient. The most conventional options of cancer treatment are surgery, radiation therapy, and chemotherapy. Surgery plays a central role in the diagnosis and treatment of cancer. Typically, a surgical approach is required for biopsy and the removal of cancerous growth. However, if the cancer has metastasized and is widespread, surgery is unlikely to result in a cure, and an alternate approach must be taken. Side effects of surgery include diminished structural or organ function and increased risk of infection, bleeding, or coagulation related complications. Radiation therapy, chemotherapy, and immunotherapy are alternatives to surgical treatment of cancer (Mayer, 1998; Ohara, 1998; Ho et al., 1998). Radiation therapy involves a precise aiming of high energy radiation to destroy cancer cells and, much like surgery, is mainly effective in the treatment of non-metastasized, localized cancer cells. Side effects of radiation therapy include skin irritation, difficulty swallowing, dry mouth, nausea, diarrhea, hair loss and loss of energy (Curran, 1998; Brizel, 1998).

Chemotherapy, the treatment of cancer with anti-cancer drugs, is another mode of cancer therapy. The effectiveness of a given anti-cancer drug therapy often is limited by the difficulty of achieving drug delivery throughout solid tumors (El-Kareh and Secomb, 1997). Chemotherapeutic strategies are based on tumor tissue growth, wherein the anti-cancer drug is targeted to the rapidly dividing cancer cells. Most chemotherapy approaches include the combination of more than one anti-cancer drug, which has proven to increase the response rate of a wide variety of cancers (U.S. Pat. No. 5,824,348; U.S. Pat. No. 5,633,016 and U.S. Pat. No. 5,798,339). A major side effect of chemotherapy drugs is that they also affect normal tissue cells, with the cells most likely to be affected being those that divide rapidly (i.e., bone marrow, gastrointestinal tract, reproductive system and hair follicles). Other toxic side effects of chemotherapy drugs are sores in the mouth, difficulty swallowing, dry mouth, nausea, diarrhea, vomiting, fatigue, bleeding, hair loss, and infection.

Immunotherapy, a rapidly evolving area in cancer research, is yet another option for the treatment of certain types of cancers. For example, the immune system identifies tumor cells as being foreign, and thus they are targeted for destruction by the immune system. Unfortunately, the response typically is not sufficient to prevent most tumor growths. However, recently there has been a focus in the area of immunotherapy to develop methods that augment or supplement the natural defense mechanism of the immune system. Examples of immunotherapies currently under investigation or in use are immune adjuvants (i.e., *Mycobacterium bovis, Plasmodium falciparum*, dinitrochlorobenzene and aromatic compounds) (U.S. Pat. No. 5,801,005; U.S. Pat. No. 5,739,169; Hui and Hashimoto, 1998; Christodoulides et al., 1998), cytokine therapy (i.e., interferons $\alpha$, $\beta$ and $\gamma$; IL-1, GM-CSF and TNF) (Bukowski et al., 1998; Davidson et al., 1998; Hellstrand et al., 1998) gene therapy (i.e., TNF, IL-1, IL-2, p53) (Qin et al., 1998; Austin-Ward & Villaseca, 1998; U.S. Pat. No. 5,830,880 and U.S. Pat. No. 5,846,945) and monoclonal antibodies (i.e., anti-ganglioside GM2, anti-HER-2, anti-p185) (Pietras et al., 1998; Hanibuchi et al., 1998; U.S. Pat. No. 5,824,311).

Yet further, viral therapy has been suggested as a potential oncolytic agent. The most commonly used oncolytic viruses are based on mutant strains of herpes simplex virus, adenovirus, and reovirus. Specifically, the E1B gene-attenuated adenovirus ONYX-015, which targets cancer cells lacking functional tumor suppressor protein p53 (Bischoff et al., 1996), the avian Newcastle disease virus, which also appears to target the N-ras oncogene in tumor cells (Lorence et al., 1994) and a genetically altered herpes simplex virus designed to target cancer cells with a dysfunction p16/pRB tumor suppressor pathway (Chase et al., 1998). Recently, reovirus has been shown to have oncolytic capacity in cells containing an activated ras pathway (Coffey et al., 1998, U.S. Pat. No. 6,136,307; U.S. Pat. No. 6,110,461).

BRIEF SUMMARY OF THE INVENTION

It is, therefore, an objective of the present invention to provide a pharmaceutical composition comprising a Reoviridae virus conjugated to a hydroxylated hydrocarbon dispersed in a pharmaceutically acceptable carrier. The preferred hydroxylated hydrocarbon is polyethylene glycol (PEG). It is well known in the art that PEG is available in a wide range of molecular weights, i.e., PEG 200–PEG 9000. In specific embodiments, it is preferred that the PEG have an average molecular weight of at least 2000. More preferably, it is envisioned that the average molecular weight of PEG is within the molecular weight range of 3000 to 7000, such as, for example, PEG 3000 to PEG 5000 is preferred, PEG 5000 to PEG 7000 is more preferred and PEG 5000 to PEG 6000 is even more preferred.

Conjugation of a hydroxylated hydrocarbon to a virus reduces the immunological properties of the virus and increases the virus survival in the bloodstream (half-life). It is contemplated that the most desirable state of conjugation of the virus which leads to the most desirable result is a state of complete conjugation or complete saturation or encapsulation of the virus. As used herein "complete conjugation", "complete saturation" or "encapsulation of the virus" refers to a state of conjugation in which almost all of the available viral chemical target amino acid residues (for example lysine residues) on the surface of the virus are conjugated to a hydroxylated hydrocarbon. It is also envisioned that one may achieve a desirable result with less than complete saturation of the target (lysine) residues on the virus. Accordingly, it is preferable that the percent range of saturation of the target (lysine) residues result in a desirable result and such range may be 35–99% or any range derivable herein, such as, 40–99% is particularly preferred, 50–99% is more preferred, 60–90% is more preferred, 70–99% is more preferred, 80–99% is even more preferred and 85–99% is even more preferred.

Members of the family Reoviridae include, but are not limited to the genera of Reovirus, Orbivirus, Rotavirus or Coltivirus. In specific embodiments, the Reoviridae virus is a reovirus. Yet further, the reovirus may be a mammalian reovirus, an avian reovirus or another reoviruses, for example, Nelson Bay virus. Specifically, the reovirus may be a human reovirus. Human reoviruses may include, but are not limited to human serotype 1 reovirus, human serotype 2 reovirus or human serotype 3 reovirus. In specific embodiments, the human reovirus is human serotype 3 reovirus.

In further embodiments, the pharmaceutical composition may further comprise a cell-targeting moiety, such as an antibody or a vascular endothelial penetration peptide. Antibodies that may be used as cell targeting moieties include, but are not limited to C225 (anti-epidermal growth factor), Trastuzuab (Hercepten), ID5 (anti-erbB-2), PB3 (anti-erbB-2), TA-1 (anti-erbB-2), 4d5 (anti-Her2/neu), Edrecolomab (anti-EpCAM), CC49 (anti-colorectal Mc5 (anti-breast carcinoma), N901 (anti-alphaNCAM), CD56, MDX447 (anti-Fc and anti-Egfr), HMFG1 (anti-MUCI), IDEC-C2B8 (anti-CD20) or viral peptides such as HPV1612. Exemplary vascular endothelial penetration peptides include, but are not limited to fibronectin attachment protein (epithelia), alpha syndecin-1 (epithelia), or viral peptides such as HPV16L2.

It is also an object of the present invention to provide a pharmaceutical composition comprising a Reoviridae virus conjugated to a polycationic polymer dispersed in a pharmaceutically acceptable carrier. The polycationic polymer is polyethylene imine. Exemplary polycationic polymers include, but are not limited to polylysine, polyetheneimine, polyhistidine, protamine, polyvinylamines, polyvinylpyridine, polymethacrylates, and polyomithine.

It is also an object of the present invention to provide a method of treating a hyperproliferative disorder comprising administering to a patient an effective amount of a Reoviridae virus conjugated to a hydroxylated hydrocarbon that is effective to treat the hyperproliferative disorder. It is preferable that the patient is human. It is also contemplated that the patient be non-human.

In specific embodiments, the virus is administered via an alimentary route or a parenteral route. Specific examples of alimentary routes include, but are not limited to oral, buccal, rectal and sublingual. The parenteral route may be intravenous, intra-tumoral or intraperitoneal. Yet further, other parenteral routes may be used for example, but not limited to, intracerebral, intratracheally, intramuscularly, endoscopically, intralesionally, percutaneously, subcutaneously, regionally, or by direct injection or perfusion. It is further contemplated that treatment methods may involve multiple administrations.

In certain embodiments, the virus is administered to a patient in an effective amount. It is envisioned that an effective amount is the amount effective to treat the hyperproliferative disease, to lyse the hyperproliferating cells or to inhibit metastasis. The effective amount is from about $10^4$, $10^5$, $10^6$, $10^7$, $10^8$, $10^9$, $10^{10}$, $10^{11}$, $10^{12}$, $10^{13}$, $10^{14}$, $10^{15}$ pfu/kg and higher and more preferably $10^6$ to $10^{12}$ pfu/kg and higher. Plaque Forming Unit (pfu) refers to live virus particles. Alternatively, the effective amount or dosage may be expressed in units of viral particles (vp); thus, the numbers listed above in "pfu" units may be expressed in units of "vp" units or "viral particles". It is contemplated that about $10^5$ to about $10^{15}$, about $10^6$ to about $10^{15}$, $10^7$ to about $10^{13}$ or $10^7$ to about $10^{15}$ viral particles/kg may be administered to a patient.

In certain embodiments, the hyperproliferative disease is further defined as cancer. The cancer comprises a neoplasm. In still further embodiments, the neoplasm is melanoma, non-small cell lung, small-cell lung, lung, hepatocarcinoma, retinoblastoma, astrocytoma, gliobastoma, squamous cell, gum, tongue, head and neck, leukemia, neuroblastoma, head, neck, breast, pancreatic, prostate, renal, bone, testicular, ovarian, mesothelioma, cervical, gastrointestinal, lymphoma, brain, colon, bladder, or other malignant or benign neoplasms.

In further embodiments, the hyperproliferative disease is rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions, carcinoma in situ, oral hairy leukoplakia, or psoriasis.

In some embodiments of the present invention a chemotherapeutic agent, radiotherapy, hormonal therapy, surgery or immunotherapy may be administered to the patient in combination with the Reoviridae virus treatment.

Another embodiment provides for a method of treating a hematopoietic neoplasm comprising administering to a patient an effective amount of a Reoviridae virus conjugated to a hydroxylated hydrocarbon that is effective to treat the hematopoietic neoplasm. The hematopoietic neoplasm is selected from the group consisting of acute myelogenous leukemia, acute lymphoblastic leukemia, myelodysplastic syndrome, chronic myelomonocytic leukemia, juvenile myelomonocyte leukemia, multiple myeloma, chronic lymphocytic leukemia or other malignancy of hematologic origin.

A further embodiment of the present invention provides a method of treating a hyperproliferative disorder comprising administering to a patient an effective amount of a Reoviridae virus conjugated to a polycationic polymer that is effective to treat the hyperproliferative disorder.

While in further embodiments, it is provided a method of lysing hyperproliferating cells comprising administering to a patient an effective amount of a Reoviridae virus conjugated to a hydroxylated hydrocarbon that is effective to lyse the hyperproliferating cells. It is contemplated that an amount effective to lyse the hyperproliferating cells means that the amount results in at least 10% lysis of the hyperproliferating cells, more preferably the amount results in at least 50% lysis and most preferably the amount results in 75% or more cell lysis. The percentage of cell lysis may be determined for tumor cells by measuring the reduction in the size of the tumor in the patient or the lysis of the tumor cells in vitro.

In still further embodiments, it is provided a method of treating a neoplasm comprising administrating an effective amount of a Reoviridae virus conjugated to a hydroxylated hydrocarbon and a targeting moiety that is effective to treat the neoplasm. The neoplasm is a solid neoplasm. The targeting factor is an antibody, a vascular endothelial penetration peptide, or a viral or microorganism derived protein or peptide that is used by the microbe to penetrate or target specific epithelia. Such an example is the human papillomavirus 16 derived "HPV16L2" peptide, a fragment of the minor capsid protein L2. In addition, laminin 5 gamma 2 chain fragments may serve as penetration factors since they are associated with tissue remodeling and the advancing edge of some tumors. These peptides appear to target and facilitate the penetration of human squamous epithelia. It is envisioned that this peptide may be used to facilitate the targeting of Reoviridae virus composition to squamous epithelial cancers. It also is contemplated that the addition of a targeting moiety may enhance the ability to treat solid neoplasm. For example, an endothelial penetration peptide may assist a parenterally (i.e., intravascular, intravenous, intraperitoneal or intracerebral) administered Reoviridae virus composition to cross the endothelial barriers to reach the tissue target.

In another embodiment, it is provided a method of inhibiting metastasis of a neoplasm in an patient comprising administering an effective amount of a Reoviridae virus conjugated to a hydroxylated hydrocarbon that is effective to inhibit metastasis.

Yet further, another embodiment of the present invention provides a method of treating a patient with cancer comprising administering to the patient an effective amount of a Reoviridae virus conjugated to a hydroxylated hydrocarbon and administering at least one other anticancer treatment. The anticancer treatment is chemotherapy, immunotherapy, surgery, or radiotherapy.

In further embodiments, it is envisioned that the Reoviridae virus composition may be administered to a patient suspected of having a hyperproliferative disorder. Specifically, the patient is suspected of harboring some residual hyperproliferative cells. Yet further, a patient that harbors residual hyperproliferative cells may have been diagnosed with a hyperproliferative disorder or has been previously diagnosed with a hyperproliferative disorder or a tumor has been resected surgically.

Yet further, as used herein, the use of the word "a" or "an" when used in conjunction with the term "comprising" in the claims and/or the specification may mean "one," but it is also consistent with the meaning of "one or more," "at least one," and "one or more than one."

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

A. Reoviridae

Figure 1:
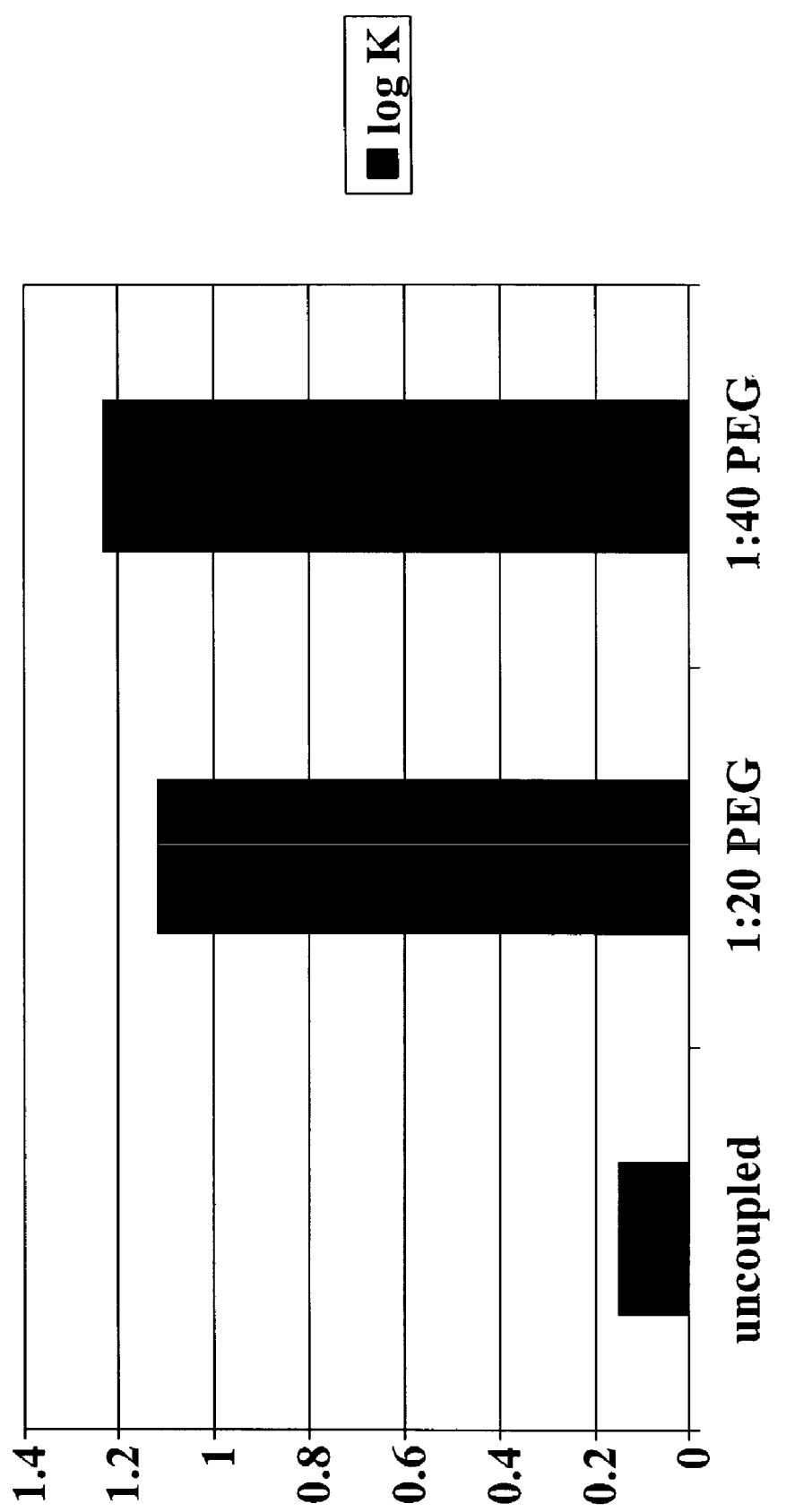
FIG. 1. This figure illustrates the saturation of PEG coupling to the virus based upon partitioning rations.

Beginning in 1959, viruses that were typically isolated from the respiratory and gastrointestinal tracts and not associated with any known disease state were classified as reovirus (Respiratory, Enteric, Orphan Viruses) (Sabin, 1959). During the 1970s, the family enlarged and currently constitutes nine genera. The general characteristics of the Reoviridae family are nonenveloped, 70 to 85 nm in diameter, double protein capsid shell, nearly spherical icosahedron shape, and 10–12 segmented doubled-stranded RNA genome (dsRNA). Of the nine genera, four genera, which includes Orthoreovirus, Orbivirus, Rotavirus and Coltivirus, infect humans. These viruses have similar structural features, nucleic acid type and composition, and replicative strategies.

The Reoviridae viruses are resistant to solvents, quaternary ammonium salts, phenol, alcohol, pH and heat (50° C. for 1 hr). The viruses survive pasteurization and the most common human strains are also the most common bovine strains. Although Reoviridae viruses are not known to be associated with any particular disease, many people have been exposed to Reoviridae viruses by the time they reach adulthood (i.e., fewer than 25% in children <5 years old, to greater than 50% in those 20–30 years old (Jackson & Muldoon, 1973; Stanley, 1974). Thus, one skilled in the art recognizes that this exposure results in native antibodies, which are present in the serum of humans.

Control of the Reoviridae virus is accomplished at the cellular level by a constitutively expressed dsRNA dependent protease that specifically inactivates EF2 through a series of kinases when it recognizes double stranded RNA (Thomis & Samuel, 1993; Yue & Shatkin, 1997). Thus the normal mode of viral transmission for Reoviridae viruses probably depends on the virus surviving in the environment and surviving passage through the gut and subsequently finding a few permissive rapidly dividing cells in the new host gut. In these cells, the virus replicates to a lytic endpoint. With so few cells involved, symptoms do not result. The viruses are shed into the environment to complete the cycle (Neutra, 1999). It is important to note that the virus has no latent state—if the virus is not blocked intracellularly replication progresses invariably to cell lysis—the only mechanism of viral release.

1. Reovirus

Of particular interest to the present invention is the use of an Orthoreovirus. It is well known to those of skill in the art that the common name for the family Reoviridae and for the specific genus Orthoreovirus is simply reovirus. Thus, in the present invention, the term "reovirus" is all inclusive of the genus Orthoreovirus and all of the viruses contained within this genus, for example, but not limited to mammalian reovirus, avian reovirus, and Nelson Bay virus.

In this genus, the virions measure 60–80 nm in diameter and possess two concentric capsid shells, each of which is icosahedral. The genome consists of double-stranded RNA in 10–12 discrete segments with a total genome size of 16–27 kbp. The 11 translated proteins accomplish at least 30 structural and enzymatic functions.

Mammalian reoviruses are ubiquitous agents that infect a variety of mammalian species. Although mammalian reoviruses share a common group antigen, three serotypes were identified by neutralization and hemagglutination-inhibition tests. These serotypes were isolated from humans and are as follows: type 1 (strain Lang), type 2 (strain Jones) and type 3 (strain Dearing or strain Abney) (Sabin, 1959; Fields, 1996).

Yet further, it is contemplated that the reovirus may be naturally occurring. The term "naturally-occurring" refers to a reovirus that has been isolated from a source in nature and has not been intentionally modified by humans in the laboratory. For example, the reovirus can be from a "field source", such as from a human patient.

2. Other Reoviridae Viruses

It is also contemplated that the species in the genus Rotavirus may be used in the present invention. It is well known that rotaviruses and reoviruses share common morphologic and biochemical properties. Thus, it is within the scope of the present invention that rotaviruses may also be used.

Yet further, the scope of the present invention is not limited to the genera Orthoreovirus and Rotavirus, the present invention also includes the use of other viruses that are classified as a Reoviridae virus and has similar morphologic and biochemical properties as a reovirus.

3. Reoviridae Infectivity of Cells

For mammalian reoviruses, the cell surface recognition signal is sialic acid (Armstrong et al., 1984; Gentsch & Pacitti, 1985; Paul et al., 1989). Due to the ubiquitous nature of sialic acid, reovirus binds efficiently to a multitude of cell lines and as such can potentially target many different tissues; however, there are significant differences in susceptibility to reovirus infection between cell lines.

As described herein cells which are resistant to reovirus infection became susceptible to reovirus infection when transformed by a gene in the Ras pathway. "Resistance" of cells to reovirus infection indicates that infection of the cells with the virus did not result in significant viral production or yield. Cells that are "susceptible" are those that demonstrate induction of cytopathic effects, viral protein synthesis, and/or virus production. Resistance to reovirus infection was found to be at the level of gene translation, rather than at early transcription. It is contemplated that the viral gene transcription in resistant cells is correlated with phosphorylation of an approximately 65 kDa cell protein, determined to be double-stranded RNA-activated protein kinase (PKR), that was not sufficiently phosphorylated in transformed cells (See U.S. Pat. Nos. 6,136,307 and 6,110,461 incorporated herein by reference). Thus, it is contemplated that reovirus reproduces by using the host cell's Ras pathway machinery in combination with an associated downregulation of PKR.

B. Reoviridae Modification

In embodiments of the present invention the Reoviridae virus is modified to reduce or eliminate an immune reaction to the Reoviridae virus. Such modifications may include packaging of the Reoviridae virus in a liposome, a micelle or other vehicle to mask the Reoviridae virus from the immune system. Alternatively, the outer capsid of the Reoviridae virion particle may be removed since the proteins present in the outer capsid are the major determinant of the host humoral and cellular responses.

As used herein the term "modified virus" refers to a Reoviridae virus that has been modified using any of the techniques described herein. Specifically, the modified virus still retains infectivity and is capable of replicating which results in cell lysis.

1. Conjugation of Hydroxylated Hydrocarbon

In particular embodiments, the present invention conjugates a hydroxylated hydrocarbon to a Reoviridae virus. As used herein, the term "hydroxylated hydrocarbon" refers to a hydrocarbon that has been hydroxylated such that a hydroxy (—OH) group has been added to at least one or more of the carbons atoms in the hydrocarbon molecule. The hydrocarbon may also be fully hydroxylated. General examples of hydroxylated hydrocarbons include, but are not limited to natural and synthetic homopolymers, such as polyols, polycarboxyl acids, hydroxylates of polycarbonyls, polyhydroxy aldehyde, polyhydroxy ketone, or polysaccharides.

Specific examples of suitable hydroxylated hydrocarbons or suitable substrates that may be transformed into hydroxylated hydrocarbons include, but are not limited to polyalkylene oxides (PAO), such as polyalkylene glycols (PAG), including polyethylene glycols (PEG), methoxypolyethylene glycols (mPEG) and polypropylene glycols, PEG-glycidyl ethers (Epox-PEG), PEG-oxycarbonylimidazole (CDI-PEG), Branched PEGs, poly-vinyl alcohol (PVA), polycarboxylates, polyvinylpyrolidone, polyethylene-co-maleic acid anhydride, polystyrene-co-malic acid anhydride, carbohydrates including mannose and galactose, dextrans including carboxymethyl-dextrans, heparin, homologous albumin, celluloses, including methylcellulose, carboxymethylcellulose, ethylcellulose, hydroxyethylcellulose carboxyethylcellulose and hydroxypropylcellulose, hydrolysates of chitosan, starches such as hydroxyethyl-starches and hydroxy propyl-starches, glycogen, agaroses and derivatives thereof, guar gum, pullulan, inulin, xanthan gum, carrageenin, pectin, alginic acid hydrolysates and bio-polymers. One skilled in the art realizes that any of the above listed substrates may be transformed using known methods (i.e., hydrolysis) in the art to effect the oxidation states of the substrates resulting in a hydroxylated hydrocarbon that may be used in the present invention.

Preferred hydroxylated hydrocarbons are non-toxic molecules such as polyethylene glycol which further requires a relatively simple chemistry for its covalent coupling to free lysine groups on the viral surface. It is well known in the art that PEG is available in a wide range of molecular weights, i.e., PEG 200–PEG 9000. In specific embodiments, it is preferred that the PEG have an average molecular weight of at least 2000. More preferably, it is envisioned that the average molecular weight of PEG is within the molecular weight range of 3000 to 7000, such as, for example, PEG 3000 to PEG 5000 is preferred, PEG 5000 to PEG 7000 is more preferred and PEG 5000 to PEG 6000 is even more preferred.

PEG modification is a well-established technique for modification of therapeutic peptides and proteins. PEGylation requires, in general, activation of hydroxyl groups of PEG with a suitable reagent that can be fully substituted by nucleophilic groups, such as lysine groups in the viral structure or protein. A variety of PEGylation methods have been developed, for example, cyanuric chloride-activated mono-methoxypolyethylene glycol (MPEG) couples to proteins via a triazine ring (Abuchowski et al., 1977) or succinimidyl succinate PEG (SS-MPEG) reacts with amino groups on the target protein using the N-hydroxysuccinimidyl (NHS)-active ester of PEG succinate (Abuchowski et al., 1984) or tresyl-MPEG (TMPEG) which reacts preferentially with the $\epsilon$-amino terminal of lysine residues (Delgado et al., 1990; Francis et al., 1998). PEG may also be linked to proteins using sulfhydryl linkages or non-covalent linkages (i.e., biotin strepaviden coupling).

Conjugation of a hydroxylated hydrocarbon to a virus reduces the immunological properties of the virus and increases the half-life of the virus. It is contemplated that the most desirable state of conjugation of the virus which leads to the most desirable result is a state of complete conjugation or complete saturation or encapsulation of the virus. As used herein "complete conjugation", "complete saturation" or "encapsulation of the virus" refers to a state of conjugation in that most all of the available viral chemical target amino acid residues (for example lysine residues) on the surface of the virus are conjugated to a hydroxylated hydrocarbon. It is also envisioned that one may achieve a desirable result with less than complete saturation of the target (lysine) residues on the virus. Accordingly, it is preferable that the percent range of saturation of the target (lysine) residues result in a desirable result and such range may be 35–99% or any range derivable herein, such as, 40–99% is particularly preferred, 50–99% is more preferred, 60–90% is more preferred, 70–99% is more preferred, 80–99% is even more preferred and 85–99% is even more preferred.

2. Conjugation of Polycationic Polymer

Another preferred embodiment of the present invention, is a polycationic polymer conjugated to a Reoviridae virus. The term "polycationic polymer" as used herein is defined as a water-soluble positively charged compound. Exemplary polycationic polymers include, but are not limited to, polylysine, polyethyleneimine (PEI), polyhistidine, protamine, polyvinylamines, polyvinylpyridine, polymethacrylates, polyornithine, or mixed ionic polymers, i.e., polyglutamate.

In specific embodiments, the preferred polycationic polymer is PEI. PEI chemistry is similar to the chemistry involved in PEGylation, thus one of skill in the would be able to substitute PEI for PEG resulting in a Reoviridae virus that comprises PEI. Similar to the hydroxylated hydrocarbon, the amount of conjugated polycationic polymer is an amount sufficient to provide a desirable result in that the virus has reduced immunological properties and increased half-life. In addition to increasing half-life of the virus, it is contemplated that PEI may also increase specific receptor driven uptake or endocytosis. It is also envisioned that the virus may be conjugated to saturation or completion or have a percent range of polycationic polymers on the virus. Accordingly, it is preferable that the percent range of polycationic polymers on the virus result in a desirable result and such range may be 35–99% or any range derivable herein, such as, 40–99% is particularly preferred, 50–99% is more preferred, 60–90% is more preferred, 70–99% is more preferred, 80–99% is even more preferred and 85–99% is even more preferred. Yet further, the amount of polycationic polymers may depend upon the properties of the polymer.

3. Other Modifications

In still further embodiments, it is contemplated that the composition of the present invention may be further modified to comprise a targeting factor, such as an antibody or a vascular endothelial penetration peptide, or other targeting peptide such as a viral derived peptide used in adsorption to specific cell types. One skilled in the art realizes that these targeting factors can increase the specificity of the composition. Yet further, the addition of the endothelial penetration peptide will enable the composition to cross through the endothelial barrier, thus escaping the circulatory system and moving into the target tissue.

Yet further, the Reoviridae virus may be a recombinant Reoviridae virus from two or more types of reoviruses with differing pathogenic phenotypes such that it contains different antigenic determinants thereby reducing or preventing an immune response by a mammal previously exposed to a reovirus subtype. Such recombinants may also reduce or modify the toxicity profile of the reovirus agent. Recombinant virions can be generated by co-infection of mammalian cells with different subtypes of Reoviridae virus with the resulting resorting and incorporation of different subtype coat proteins into the resulting virion capsids. The proteins may be mutated by replacement, insertion or deletion. Such mutations may be generated by methods known in the art, such as site directed mutagenesis.

4. Viral Purification

It may be desirable to purify the Reoviridae virus, modified virus or variants thereof. Purification techniques are well known to those of skill in the art. Analytical methods particularly suited to the preparation of a pure viral batch are tangential flow concentration or cesium chloride ultra-centrifugation (January, 1971).

Certain aspects of the present invention concern the purification, and in particular embodiments, the substantial purification, of the modified virus. The term "purified modified virus" as used herein, is intended to refer to a virus or viral batch or viral stock that is purified to any degree relative to its naturally-obtainable state.

Generally, "purified" will refer to a virus or viral batch or viral stock that has been subjected to fractionation to remove various other components, such as unreactive PEG, and which composition substantially retains its expressed biological activity. Where the term "substantially purified" is used, this designation will refer to a composition in which the virus or viral batch or viral stock forms the major component of the composition, such as constituting about 70% or more of the virus or viral batch or viral stock in the composition.

Yet further, the virus can be purified by affinity purification with elution at low pH. The virus is then concentrated by saturated ammonium sulfate and dialyzed by tangential flow to remove small molecules.

Various methods for quantifying the degree of purification of the virus or viral batch or viral stock will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the virus or viral batch or viral stock exhibits a detectable activity. In specific embodiments, the tissue infective dose (TID) per unit protein of the crude cell lysate is calculated and compared to the TID/protein ratio of the purified viral fraction and to the TID/protein ratio following cesium chloride gradient purification.

C. Treatment of Hyperproliferative Disease

In the present invention, the modified virus, which has been modified to reduce immunogenicity and increase stability in the circulation, is administered to a patient that suffers from a hyperproliferative disease or disorder. A "hyperproliferative disease" is any disease or disorder in which the cells proliferate more rapidly than normal tissue growth, or in which cell growth is not properly regulated. Thus, a "hyperproliferating cell" is a cell that is hyperproliferating more rapidly than normal cells, or one that can not be blocked from replication at certain steps in the cell cycle.

The hyperproliferative disease, includes but is not limited to neoplasms. A neoplasm is an abnormal tissue growth, generally forming a distinct mass, that grows by cellular hyperproliferation more rapidly, or in an unregulated manner relative to normal tissue growth. Neoplasms show partial or total lack of structural organization and functional coordination with normal tissue. These can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoietic structures (structures pertaining to the formation of blood cells) including components of the immune system, are called leukemias and lymphomas. A tumor is the neoplastic growth of the disease cancer. As used herein, a "neoplasm", also referred to as a "tumor", is intended to encompass hematopoietic neoplasms as well as solid neoplasms. Examples of neoplasms include, but are not limited to melanoma, non-small cell lung, small-cell lung, lung hepatocarcinoma, retinoblastoma, astrocytoma, gliobastoma, gum, tongue, leukemia, neuroblastoma, head, neck, breast, pancreatic, prostate, renal, bone, testicular, ovarian, mesothelioma, cervical, gastrointestinal, lymphoma, brain, colon, bladder, or other malignant or benign neoplasms. Other hyperproliferative diseases include, but are not limited to neurofibromatosis is rheumatoid arthritis, Waginer's granulomatosis, Kawasaki's disease, lupus erathematosis, midline granuloma, inflammatory bowel disease, osteoarthritis, leiomyomas, adenomas, lipomas, hemangiomas, fibromas, vascular occlusion, restenosis, atherosclerosis, pre-neoplastic lesions, carcinoma in situ, oral hairy leukoplakia, or psoriasis, and pre-leukemias, anemia with excess blasts, and mylodysplastic syndrome.

Some of the cells of a hyperproliferative disorder may have a mutation in which the ras gene (or an element of the Ras signaling pathway) is activated, either directly (i.e., by an activating mutation in ras) or indirectly (i.e., by activation of an upstream or downstream element in the Ras pathway). Activation of an upstream element in the Ras pathway includes, for example, transformation with epidermal growth factor receptor (EGFR) or Sos. Activation of a downstream element in the Ras pathway includes, for example, Map Kinases, Raf, jun/fos. A hyperproliferative disease that results, at least in part, by the activation of Ras, an upstream or downstream element of Ras, or an element in the Ras signaling pathway is referred to herein as a "Ras-mediated proliferative disorder". Yet further, other pathways that activate MAPKK, MAPKKK, or constitutively activate cell cycling are also potential targets for reoviral mediated therapy.

Particular neoplasms of interest in the present invention include, but are not limited to hematopoietic neoplasms. For example, a hematopoietic neoplasm may include acute myelogenous leukemia, acute lymphoblastic leukemia, myelodysplastic syndrome, chronic myelomonocytic leukemia, juvenile myelomonocyte leukemia, multiple myeloma, chronic lymphocytic leukemia or other malignancy of hematologic origin.

In still further embodiments, it is contemplated that the composition of the present invention may be further modified to comprise a targeting factor, such as an antibody or a vascular endothelial penetration peptide or other targeting peptide. This further modified composition may be administered to a patient systemically (i.e., intravenous, intraperitoneal, or intrathecal) to treat or target specific tumors, such as solid tumors. One skilled in the art realizes that these targeting factors can increase the specificity of the composition. Yet further, the addition of the endothelial penetration peptide will enable the composition to cross through the endothelial barrier, thus escaping the circulatory system and moving into the target tissue. Antibodies that may be used as cell targeting moieties include, but are not limited to C225 (anti-epidermal growth factor), Trastuzuab (Hercepten), ID5 (anti-erbB-2), PB3 (anti-erbB-2), TA-1 (anti-erbB-2), 4d5 (anti-Her2/neu), Edrecolomab (anti-EpCAM), CC49 (anti-colorectal), Mc5 (anti-breast carcinoma), N901 (anti-alphaNCAM), CD56, MDX447 (anti-Fc and anti-Egfr), HMFG1 (anti-MUCI), IDEC-C2B8 (anti-CD20) or viral peptides such as HPV1612. Exemplary vascular endothelial penetration peptides include, but are not limited to fibronectin attachment protein (epithelia), alpha syndecin-1 (epithelia). Exemplary tissue targeting factors include, but are not limited to viral or microbial derived adhesion or adsorption factors such as viral peptide HPV16L2. It is also contemplated that other tissue targeting factors may also be used to target the virus to specific tissues or tumors, for example, laminin 5 gamma 2 chain fragments.

It is also contemplated that the present invention may be administered to a patient to inhibit metastasis of a hyperproliferative disease.

D. Combination Treatments

In order to increase the effectiveness of the Reoviridae virus composition of the present invention, it may be desirable to combine these compositions with other agents effective in the treatment of hyperproliferative disease, such as anti-cancer agents, or with surgery. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. Anti-cancer agents include biological agents (biotherapy), chemotherapy agents, and radiotherapy agents. More generally, these other compositions would be provided in a combined amount effective to kill or inhibit proliferation of the cell. This process may involve contacting the cells with Reoviridae virus composition construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the Reoviridae virus composition and the other includes the second agent(s).

Tumor cell resistance to chemotherapy and radiotherapy agents represents a major problem in clinical oncology. One goal of current cancer research is to find ways to improve the efficacy of chemotherapy, radiotherapy, surgery, immunotherapy, or gene therapy is by combining it with viral oncolytic therapy. For example, the herpes simplex-thymidine kinase (HS-tK) gene, when delivered to brain tumors by a retroviral vector system, successfully induced susceptibility to the antiviral agent ganciclovir (Culver et al., 1992). In the context of the present invention, it is contemplated that Reoviridae virus composition could be used similarly in conjunction with chemotherapeutic, radiotherapeutic, immunotherapeutic or other biological intervention, in addition to other pro-apoptotic or cell cycle regulating agents.

Toxicity of chemotherapy, immunotherapy, radiotherapy, is a major problem in cancer management. One goal of the current cancer research is to find more specific anti-tumor activities with less general systemic toxicity. The high activity of reovirus replication in tumor cells and the low or absent ability to replicate in normal tissue may lead to a high therapeutic index for the current embodied invention. Furthermore, since the virus is controlled at the cellular level, an intact immune system is not needed. Thus, this therapy may be particularly useful in patients who have experienced toxicity from prior myelosupressive treatment.

Alternatively, the Reoviridae virus composition may precede or follow the other agent treatment by intervals ranging from minutes to weeks. In embodiments where the other agent and Reoviridae virus composition are applied separately to the cell, one would generally ensure that a significant period of time did not expire between the time of each delivery, such that the agent and Reoviridae virus composition would still be able to exert an advantageously combined effect on the cell. In such instances, it is contemplated that one may contact the cell with both modalities within about 12–24 h of each other and, more preferably, within about 6–12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, Reoviridae virus composition is "A" and the secondary agent, such as radio- or chemotherapy or immunotherapy or gene therapy, is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A

B/A/B/A B/A/A/B A/A/A/B B/A/A/A A/B/A/A A/A/B/A

Administration of the therapeutic Reoviridae virus compositions of the present invention to a patient will follow general protocols for the administration of chemotherapeutics, taking into account the toxicity, if any, of the Reoviridae virus composition. It is expected that the treatment cycles would be repeated as necessary. It also is contemplated that various standard therapies, as well as surgical intervention, may be applied in combination with the described hyperproliferative cell therapy.

1. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicamycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristine, vinblastine and methotrexate, Temozolomide (an aqueous form of DTIC), or any analog or derivative variant of the foregoing. The combination of chemotherapy with biological therapy is known as biochemotherapy.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which the Reoviridae virus composition and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

3. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. Apoptotic tumor cells are scavenged by reticuloendothelial cells including dendritic cells and macrophages and presented to the immune system to generate anti-tumor immunity (Rovere et al., 1999; Steinman et al., 1999).

Examples of immunotherapies currently under investigation or in use are immune adjuvants (i.e., *Mycobacterium bovis, Plasmodium falciparum*, dinitrochlorobenzene and aromatic compounds) (U.S. Pat. No. 5,801,005; U.S. Pat. No. 5,739,169; Hui and Hashimoto, 1998; Christodoulides et al., 1998), cytokine therapy (i.e., interferons α, β and γ; IL-1, GM-CSF and TNF) (Bukowski et al., 1998; Davidson et al., 1998; Hellstrand et al., 1998) gene therapy (i.e., TNF, IL-1, IL-2, p53) (Qin et al., 1998; Austin-Ward and Villaseca, 1998; U.S. Pat. No. 5,830,880 and U.S. Pat. No. 5,846,945) and monoclonal antibodies (i.e., anti-ganglioside GM2, anti-HER-2, anti-p185) (Pietras et al., 1998; Hanibuchi et al., 1998; U.S. Pat. No. 5,824,311). Herceptin (trastuzumab) is a chimeric (mouse-human) monoclonal antibody that blocks the HER2-neu receptor. It possesses antitumor activity and has been approved for use in the treatment of malignant tumors (Dillman, 1999). It is contemplated that one or more anti-cancer therapies may be employed with the Reoviridae virus composition therapy described herein.

a. Passive Immunotherapy

A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

Preferably, human monoclonal antibodies are employed in passive immunotherapy, as they produce few or no side effects in the patient. However, their application is somewhat limited by their scarcity and have so far only been administered intralesionally. Human monoclonal antibodies to ganglioside antigens have been administered intralesionally to patients suffering from cutaneous recurrent melanoma (Irie & Morton, 1986). Regression was observed in six out of ten patients, following, daily or weekly, intralesional injections. In another study, moderate success was achieved from intralesional injections of two human monoclonal antibodies (Irie et al., 1989).

It may be favorable to administer more than one monoclonal antibody directed against two different antigens or even antibodies with multiple antigen specificity. Treatment protocols also may include administration of lymphokines or other immune enhancers as described by Bajorin et al. (1988). It is envisioned that the Reoviridae virus composition of the present invention may be administered in combination with monoclonal antibodies that are used to treat cancers.

b. Active Immunotherapy

In active immunotherapy, an antigenic peptide, polypeptide or protein, or an autologous or allogenic tumor cell composition or "vaccine" is administered, generally with a distinct bacterial adjuvant (Ravindranath & Morton, 1991; Morton & Ravindranath, 1996; Morton et al., 1992; Mitchell et al., 1990; Mitchell et al., 1993). In melanoma immunotherapy, those patients who elicit high IgM response often survive better than those who elicit no or low IgM antibodies (Morton et al., 1992). IgM antibodies are often transient antibodies and the exception to the rule appears to be anti-ganglioside or anticarbohydrate antibodies.

c. Adoptive Immunotherapy

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989). To achieve this, one would administer to an animal, or human patient, an immunologically effective amount of activated lymphocytes in combination with the Reoviridae virus composition as described herein. The activated lymphocytes will most preferably be the patient's own cells that were earlier isolated from a blood or tumor sample and activated (or "expanded") in vitro.

4. Genes

In yet another embodiment, the secondary treatment is gene therapy in which a therapeutic polynucleotide is administered before, after, or at the same time the Reoviridae virus composition. Delivery of the Reoviridae virus composition with a vector encoding one of the following gene products will have a combined anti-hyperproliferative effect on target tissues. A variety of proteins are encompassed within the invention, some of which are described below. Table 1 lists various genes that may be targeted for gene therapy of some form in combination with the present invention.

a. Inducers of Cellular Proliferation

The proteins that induce cellular proliferation further fall into various categories dependent on function. The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally-occurring oncogenic growth factor. In one embodiment of the present invention, it is contemplated that anti-sense mRNA directed to a particular inducer of cellular proliferation is used to prevent expression of the inducer of cellular proliferation.

The proteins FMS, ErbA, ErbB and neu are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (i.e., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

The proteins Jun, Fos and Myc are proteins that directly exert their effects on nuclear functions as transcription factors.

b. Inhibitors of Cellular Proliferation

The tumor suppressor oncogenes function to inhibit excessive cellular proliferation. The inactivation of these genes destroys their inhibitory activity, resulting in unregulated proliferation. The tumor suppressors p53, p16 and C-CAM are described below.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as large-T antigen and E1B. The protein is found in normal tissues and cells, but at concentrations which are minute by comparison with transformed cells or tumor tissue Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the G1. The activity of this enzyme may be to phosphorylate Rb at late G1. The activity of CDK4 is controlled by an activating subunit, D-type cyclin, and by an inhibitory subunit, the p16INK4 has been biochemically characterized as a protein that specifically binds to and inhibits CDK4, and thus may regulate Rb phosphorylation (Serrano et al., 1993; Serrano et al., 1995). Since the p16INK4 protein is a CDK4 inhibitor (Serrano, 1993), deletion of this gene may increase the activity of CDK4, resulting in hyperphosphorylation of the Rb protein. p16 also is known to regulate the function of CDK6.

Other genes that may be employed according to the present invention include Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (i.e., COX-1, TFPI), PGS, Dp, E2F, ras, myc, neu, raf, erb, fms, trk, ret, gsp, hst, abl, E1A, p300, genes involved in angiogenesis (i.e., VEGF, FGF, thrombospondin, BAI-1, GDAIF, or their receptors) and MCC.

c. Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (i.e., $BCl_{XL}$, $Bcl_W$, $Bc_{LS}$, Mcl-1, A1, Bfl-1) or counteract Bcl-2 function and promote cell death (i.e., Bax, Bak, Bik, Bim, Bid, Bad, Harakiri).

5. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

6. Other Agents

It is contemplated that other agents may be used in combination with the present invention to improve the efficacy of treatment. These additional agents include immunomodulatory agents, agents that affect the up-regulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adehesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

TABLE 1

Oncogenes

| Gene | Source | Human Disease | Function |
|---|---|---|---|
| Growth Factors | | | |
| HST/KS | Transfection | | FGF family member |
| INT-2 | MMTV promoter Insertion | | FGF family member |
| INTI/WNTI | MMTV promoter Insertion | | Factor-like |
| SIS | Simian sarcoma virus | | PDGF B |
| Receptor Tyrosine Kinases | | | |
| ERBB/HER | Avian erythroblastosis Virus; ALV promoter Insertion; amplified Human tumors | Amplified, deleted Squamous cell cancer; glioblastoma | EGF/TGF-α/ Amphiregulin/ Hetacellulin receptor |
| ERBB-2/NEU/HER-2 | Transfected from rat Glioblastomas | Amplified breast, ovarian, gastric cancers | Regulated by NDF/Heregulin and EGF-Related factors |
| FMS | SM feline sarcoma virus | | CSF-1 receptor |
| KIT | HZ feline sarcoma virus | | MGF/Steel receptor Hematopoieis |
| TRK | Transfection from Human colon cancer | | NGF (nerve growth Factor) receptor |
| MET | Transfection from Human osteosarcoma | | Scatter factor/ HGF Receptor |
| RET | Translocations and point mutations | Sporadic thyroid cancer; familial medullary thyroid cancer; multiple endocrine neoplasias 2A and 2B | Orphan receptor Tyr Kinase |
| ROS | URII avian sarcoma Virus | | Orphan receptor Tyr Kinase |
| PDGF receptor | Translocation | Chronic Myelomonocytic Leukemia | TEL(ETS-like Transcription factor)/PDGF receptor gene Fusion |
| TGF-β receptor | | Colon carcinoma Mismatch mutation Target | |
| NON-RECEPTOR TYROSINE KINASES | | | |
| ABL | Abelson Mul. V | Chronic myelogenous Leukemia translocation With BCR | Interact with RB, RNA Polymerase, CRK, CBL |
| FPS/FES | Avian Fujinami SV; GA FeSV | | |
| LCK | Mul. V (murine leukemia Virus) promoter Insertion | | Src family; T cell Signaling; interacts CD4/CD8 T cells |
| SRC | Avian Rous sarcoma Virus | | Membrane-associated Tyr kinase with signaling function; activated by receptor kinases |
| YES | Avian Y73 virus | | Src family; signaling |
| SER/THR PROTEIN KINASES | | | |
| AKT | AKT8 murine retrovirus | | Regulated by PI(3)K?; Regulate 70-kd S6 k? |
| MOS | Maloney murine SV | | GVBD; cystostatic Factor; MAP kinase Kinase |
| PIM-1 | Promoter insertion Mouse | | |
| RAF/MIL | 3611 murine SV; MH2 avian SV | | Signaling in RAS Pathway |
| MISCELLANEOUS CELL SURFACE | | | |
| APC | Tumor suppressor | Colon cancer | Interacts with catenins |
| DCC | Tumor suppressor | Colon cancer | CAM domains |
| E-cadherin | Candidate tumor Suppressor | Breast cancer | Extracellular homotypic Binding; intracellular Interacts with catenins |
| PTC/NBCCS | Tumor suppressor and Drosophilia homology | Nevoid basal cell cancer Syndrome (Gorline Syndrome) | 12 transmembrane domain; signals through Gli homogue CI to antagonize Hedgehog pathway |
| TAN-1 homologue | Notch Translocation | T-ALI. | Signaling? |
| MISCELLANEOUS SIGNALING | | | |
| BCL-2 | Translocation | B-cell lymphoma | Apoptosis |
| CBL | Mu Cas NS-1 V | | Tyrosine-Phosphorylated RING Finger interact Abl |
| CRK | CT1010 ASV | | Adapted SH2/SH3 Interact Abl |
| DPC4 | Tumor suppressor | Pancreatic cancer | TGF-β-related signaling Pathway |
| MAS | Transfection and Tumorigenicity | | Possible angiotensin Receptor |

TABLE 1-continued

Oncogenes

| Gene | Source | Human Disease | Function |
|---|---|---|---|
| NCK GUANINE NUCLEOTIDE EX-CHANGERS AND BINDING PROTEINS | | | Adaptor SH2/SH3 |
| BCR | | Translocated with ABL in CML | Exchanger; protein Kinase |
| DBL | Transfection | | Exchanger |
| GSP | | | |
| NF-1 | Hereditary tumor Suppressor | Tumor suppressor Neurofibromatosis | RAS GAP |
| OST | Transfection | | Exchanger |
| Harvey-Kirsten, N-RAS | HaRat SV; Ki RaSV; Balb-MoMuSV; Transfection | Point mutations in many Human tumors | Signal cascade |
| VAV | Transfection | | S112/S113; exchanger |
| NUCLEAR PROTEINS AND TRANSCRIPTION FACTORS | | | |
| BRCA1 | Heritable suppressor | Mammary Cancer/ovarian cancer | Localization unsettled |
| BRCA2 | Heritable suppressor | Mammary cancer | Function unknown |
| ERBA | Avian erythroblastosis Virus | | Thyroid hormone Receptor (transcription) |
| ETS | Avian E26 virus | | DNA binding |
| EVII | MuLV promotor Insertion | AML | Transcription factor |
| FOS | FBI/FBR murine osteosarcoma viruses | | 1 transcription factor with c-JUN |
| GLI | Amplified glioma | Glioma | Zinc finger; cubitus Interruptus homologue is in hedgehog signaling pathway; inhibitory link PTC and hedgehog |
| HMGI/LIM | Translocation t(3:12) t(12:15) | Lipoma | Gene fusions high Mobility group HMGI-C (XT-hook) and transcription factor LIM or acidic domain |
| JUN | ASV-17 | | Transcription factor AP-1 with FOS |
| MLL/VHRX + ELI/MEN | Translocation/ fusion ELL with MLL Trithorax-like gene | Acute myeloid leukemia | Gene fusion of DNA-Binding and methyl Transferase MLL with ELI RNA pol II Elongation factor |
| MYB | Avian myeloblastosis Virus | | DNA binding |
| MYC | Avian MC29; Translocation B-cell Lymphomas; promoter Insertion avian leukosis Virus | Burkitt's lymphoma | DNA binding with MAX partner; cyclin Regulation; interact RB?; regulate Apoptosis? |
| N-MYC L-MYC | Amplified | Neuroblastoma Lung cancer | |
| REL | Avian Retriculoendo-theliosis Virus | | NF-κB family Transcription factor |
| SKI | Avian SKV770 Retrovirus | | Transcription factor |
| VHL | Heritable suppressor | Von Hippel-Landau Syndrome | Negative regulator or Elongin; transcriptional Elongation complex |
| WT-1 | | Wilm's tumor | Transcription factor |
| CELL CYCLE/DNA DAMAGE RESPONSE | | | |
| ATM | Hereditary disorder | Ataxia-telangiectasia | Protein/lipid kinase Homology; DNA Damage response Upstream in P53 Pathway |
| BCL-2 | Translocation | Follicular lymphoma | Apoptosis |
| FACC | Point mutation | Fanconi's anemia group C (predisposition Leukemia | |
| FHIT | Fragile site 3p14.2 | Lung carcinoma | Histidine triad-related Dia-denosine 5',3''''-P$^1$,p$^4$ tetraphosphate Asymmetric hydrolase |
| HMLI/MutL | | HNPCC | Mismatch repair; MutL Homologue |
| HMSH2/MutS | | HNPCC | Mismatch repair; MutS Homologue |
| HPMS1 | | HNPCC | Mismatch repair; MutL Homologue |
| HPMS2 | | HNPCC | Mismatch repair; MutL Homologue |
| INK4/MTS1 | Adjacent INK-4B at 9p21; CDK complexes | Candidate MTS1 Suppressor and MLM Melanoma gene | p16 CDK inhibitor |
| INK4B/MTS2 | | Candidate suppressor | p15 CDK inhibitor |
| MDM-2 | Amplified | Sarcoma | Negative regulator p53 |
| p53 | Association with SV40 T. antigen | Mutated >50% human Tumors, including Hereditary Li-Fraumeni Syndrome | Transcription factor; Check-point control; Apoptosis |
| PRAD1/BCL1 | Translocation with Parathyroid hormone or IgG | Parathyroid adenoma; B-CLL | Cyclin D |

TABLE 1-continued

Oncogenes

| Gene | Source | Human Disease | Function |
|---|---|---|---|
| RB | Hereditary Retinoblastoma; Association with many DNA virus tumor Antigens | Retinoblastoma; Osteosarcoma; breast Cancer; other sporadic Cancers | Interact cyclin/ cdk; Regulate E2F Transcription factor |
| XPA | | Xeroderma Pigmentosum; skin Cancer predisposition | Excision repair; photo-Product recognition; zinc finger |

E. Pharmaceutical Formulations and Delivery

In a preferred embodiment of the present invention, a method of treatment for a hyperproliferative disease by the delivery of an Reoviridae virus composition is contemplated. Hyperproliferative diseases that are most likely to be treated in the present invention are those that result from mutations in an oncogene and/or the reduced expression of a wild-type protein in the hyperproliferative cells. Examples of hyperproliferative diseases contemplated for treatment include melanoma, non-small cell lung, small-cell lung, lung hepatocarcinoma, retinoblastoma, astrocytoma, gliobastoma, gum, tongue, leukemia, neuroblastoma, head, neck, breast, pancreatic, prostate, renal, bone, testicular, ovarian, mesothelioma, cervical, gastrointestinal, lymphoma, brain, colon, bladder, or other malignant or benign neoplasms, rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions, carcinoma in situ, oral hairy leukoplakia, or psoriasis and any other hyperproliferative diseases that may be treated by administering Reoviridae virus composition.

An effective amount of the pharmaceutical composition, generally, is defined as that amount sufficient to detectably and repeatedly to ameliorate, reduce, minimize or limit the extent of the disease or its symptoms. More rigorous definitions may apply, including elimination, eradication or cure of disease.

1. Administration

To kill cells, inhibit cell growth, inhibit metastasis, decrease tumor or tissue size and otherwise reverse or reduce the malignant phenotype of tumor cells, using the methods and compositions of the present invention, one would generally contact a hyperproliferative cell with the Reoviridae virus composition. The routes of administration will vary, naturally, with the location and nature of the lesion, and include, i.e., intradermal, transdermal, parenteral, intravenous, intramuscular, intranasal, subcutaneous, percutaneous, intratracheal, intraperitoneal, intratumoral, perfusion, lavage, direct injection, and oral administration and formulation.

Intratumoral injection, or injection into the tumor vasculature is specifically contemplated for discrete, solid, accessible tumors. Local, regional or systemic administration also may be appropriate. For tumors of>4 cm, the volume to be administered will be about 4–10 ml (preferably 10 ml), while for tumors of<4 cm, a volume of about 1–3 ml will be used (preferably 3 ml). Multiple injections delivered as single dose comprise about 0.1 to about 0.5 ml volumes. The viral particles may advantageously be contacted by administering multiple injections to the tumor, spaced at approximately 1 cm intervals.

In the case of surgical intervention, the present invention may be used preoperatively, to render an inoperable tumor subject to resection. Alternatively, the present invention may be used at the time of surgery, and/or thereafter, to treat residual or metastatic disease. For example, a resected tumor bed may be injected or perfused with a formulation comprising reovirus or a reovirus-encoding construct. The perfusion may be continued post-resection, for example, by leaving a catheter implanted at the site of the surgery. Periodic post-surgical treatment also is envisioned.

Continuous administration also may be applied where appropriate, for example, where the tumor is excised and the tumor bed is treated to eliminate residual, microscopic disease. Delivery via syringe or catherization is preferred. Such continuous perfusion may take place for a period from about 1–2 hours, to about 2–6 hours, to about 6–12 hours, to about 12–24 hours, to about 1–2 days, to about 1–2 wk or longer following the initiation of treatment. Generally, the dose of the therapeutic composition via continuous infusion will be equivalent to that given by a single or multiple injections, adjusted over a period of time during which the perfusion occurs. For this oncolytic therapy however, unlike chemotherapy, much higher total doses may be possible if the perfusion is slow.

Treatment regimens may vary as well, and often depend on tumor type, tumor location, disease progression, and health and age of the patient. Obviously, certain types of tumor will require more aggressive treatment, while at the same time, certain patients cannot tolerate more taxing protocols. The clinician will be best suited to make such decisions based on the known efficacy and toxicity (if any) of the therapeutic formulations.

In certain embodiments, the tumor being treated may not, at least initially, be resectable. Treatments with the Reoviridae virus composition may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

A typical course of treatment, for a primary tumor or a post-excision tumor bed, will involve multiple doses. Typical primary tumor treatment involves a 6 dose application over a two-week period. The two-week regimen may be repeated one, two, three, four, five, six or more times. During a course of treatment, the need to complete the planned dosings may be re-evaluated.

The treatments may include various "unit doses." Unit dose is defined as containing a predetermined-quantity of the Reoviridae virus composition. The quantity to be administered, and the particular route and formulation, are within the skill of those in the clinical arts. A unit dose need not be administered as a single injection but may comprise continuous infusion over a set period of time. Unit dose of the present invention may conveniently be described in terms of plaque forming units (pfu) for a viral construct. Unit doses range from $10^7$, $10^8$, $10^9$, $10^{10}$, $10^{11}$, $10^{12}$, $10^{13}$ pfu and higher. Alternatively, depending on the kind of virus and the titer attainable, and the type of tumor and routes of administration, one will deliver $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, or $1\times10^{15}$ or higher infectious viral particles (vp) to the patient or to the patient's cells.

2. Injectable Compositions and Formulations

One preferred method for the delivery of a Reoviridae virus composition to hyperproliferative cells in the present invention is via a parenteral route. Specifically, the pharmaceutical compositions disclosed herein may be administered intravenously, intratumorally, intra-cerebrally, intradermally, intramuscularly, transdermally or even intraperitoneally as described in U.S. Pat. No. 5,543,158; U.S. Pat. No. 5,641,515 and U.S. Pat. No. 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intra-tumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "pharmaceutically acceptable carrier" includes any and all solvents, dispersion media, coatings, surfactants, antioxidants, preservatives (i.e., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289–1329, incorporated herein by reference). Except insofar as any conventional carrier is incompatible with the active ingredient, its use in the therapeutic or pharmaceutical compositions is contemplated.

3. Alimentary Compositions and Formulations

One preferred method for the delivery of a Reoviridae virus composition to hyperproliferative cells in the present invention is via an alimentary route. Specifically, the pharmaceutical compositions disclosed herein may be administered orally, buccally, rectally, or sublingually.

In certain embodiments the Reoviridae virus composition is prepared for administration by such routes as oral ingestion. In these embodiments, the solid composition may comprise, for example, solutions, suspensions, emulsions, tablets, pills, capsules (i.e., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

F. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Production of a Viral Lot

Experimental viral lots were made for human reovirus type 3 (RIII) and human reovirus type 1 (RI) from growth on L cells, PRMK cells, Hep2 cells and D104-1-1 cells.

Briefly, the cells were established at sub-confluence in a serum free/protein free medium (SigmaS2772) or DMEM or RPMI medium containing 2–10% FBS. Cells were allowed to attach and grow for 24 hrs. A RIII or RI viral aliquot frozen at −70° C. was thawed at 35° C. for 1 min. The cells were inoculated at 1 MOI, diluted in the medium. Specifically, 200 ul of inoculum containing $10^8$ PFU was applied to a 15×125 mm tube containing approximately 107 cells in 0.5 ml of serum free media. After allowing 1 to 4 hr for adsorption, 1.5 ml of additional growth media was added. Viral growth was allowed to proceed to complete cell lysis, ~72 hr to 120 hr, and cell debris was removed by centrifugation at 12,000 g for 10 min. This crude supernatant was considered an experimental lot. These lots identify the cell line that produced the highest titer of virus.

Next, the viral stock was diluted directly in media at a ratio of 1:10. Ten serial dilutions were made such that the virus was prepared in a final volume of media directly appropriate to the cell number, i.e., 200 ul into 1,800 ul media. Cell tubes were then inoculated with the viral media mixture from the dilution series. If 4 of 4 tubes at one dilution level showed complete CPE this was called 100% lysis. Similarly if 2 of 4 tubes showed CPE at (12 days allowing for two replication cycles), this dilution would be 50% CPE. Tissue culture infectious dose endpoint (TCID50) was calculated (Hsiung, 1994).

Table 2 shows the results of the analysis of the limiting dilutions. The results were rounded to the base 10 log.

TABLE 2

| Limiting dilutions | | | |
| --- | --- | --- | --- |
| Virus | Cell Line | Medium | Titer |
| RIII | PRMK | Serum Free | $10^9$ |
| RI | PRMK | Serum Free | $10^7$ |
| RIII | Hep2 | FBS 2% | $10^9$ |
| RI | Hep2 | FBS 2% | $10^9$ |
| RIII | D104-1-1 | FBS 10% | $10^8$ |
| RIII | D104-1-1 | Serum Free | $10^9$ |
| RIII | Lcell(4LMKT) | Serum Free | $10^9$ |
| RI | Lcell(4LMKT) | Serum Free | $10^8$ |

Other cell lines were tested to determine the growth of RIII and RI. RIII grew better than RI in CHO, HT29, and MRC5, but monolayer lysis was never>50% (Table 3). All media contained 2% FBS. The data illustrated in Table 3 was a semiquantitative assessment based on visual CPE on examination at 200× magnification. The pattern was further confirmed when scraped cells were examined microscopically for characteristic large intracytoplasmic inclusions by acridine orange staining.

TABLE 3

| | Growth of RI versus RIII | | | |
| --- | --- | --- | --- | --- |
| | CHO | HT29 | MRC5 | Sp2/0 |
| R I | +/− | + | ++ | ++ |
| R III | ++ | +++ | +++ | +++ |

Next, to produce sufficient viral inoculum of RIII, RIII was expanded on D104-1-1 in serum free media (McCrae, 1985). D104 cells were expanded in two 2 L roller bottles in DMEM with glycine and 5% FCS. Each roller bottle was inoculated with cells from a 75 cm flask. Cells were allowed to reach 90% confluence (approximately 4 days). The media is removed, cells were gently washed with PBS, and media was replaced with 50 ml serum free/protein free media containing 20 micro units of insulin, cortisone, and virus. Approximately $10^{10}$ virus was added to each 2 liter bottle. approximately $10^{10}$ cells were present, this results in an MOI of 1.75-ml of serum free media was added at 24 hr, 72 hr, and 96 hr. CPE was approximately 70%. 550 ml was harvested and cell debris was removed by centrifugation at 4000 g for 30 min. The supernatant was concentrated by the addition of filter sterilized room temperature saturated ammonium sulfate. (~400 ml supernatant plus 200 ml SAS). This mixture was held at RT for 30 min then centrifuged at 4000 g for 1 hr. The pellet was resuspended in 5 ml of isotonic serum free media (without insulin) and filter sterilized. This product was dialyzed in sterile dialysis membrane. The aliquots were divided and frozen at −70° C.

Example 2 pH Requirements

Polyethylene glycol (PEG) and polyethylene imide (PEI) modification chemistry usually requires an alkaline pH. The effect of alkaline pH was tested on RIII as follows.

Briefly, an RIII aliquot was diluted in RPMI medium to 100 MOI and divided 1:1. The pH was adjusted with a fixed volume of NaOH in RPMI. The control received an equal volume of RPMI. Exposure time was 10 min. Both media were neutralized with MOPS +HCl or MOPS and the samples assayed by limiting dilution on Hep2 with 2% FBS (Table 4).

TABLE 4 pH versus viral titer

| Control pH 7.0 | Hep 2 | FBS 2% | Viral titer $10^9$ |
| Test pH 9.2 | Hep 2 | FBS 2% | Viral titer $10^{11}$ |

Example 3

Development a Modified Virus

Prior to conjugating PEG to the virus, a viral batch was grown. Briefly, L cells were established at sub-confluence in a serum free/protein free medium (Sigma S2772). Cells were allowed to attach and grow for 24 hr. A RIII viral aliquot frozen at −70° C. was thawed at 35° C. for 1 min. L cells were inoculated at 10 MOI, diluted in S2772 medium. Virus was allowed to grow for 48 hrs, then 1 mCi of [$^{35}$S]-methionine was added in a minimal 6 ml volume of fresh S2772 medium. Viral growth was allowed to proceed to complete cell lysis, ~72 hr, and cell debris was removed by centrifugation at 12,000 g for 10 min. Virus was concentrated on an ethylene oxide sterilized ammicon 30 concentrator. The viral batch was dialyzed using autoclaved 18,000 mwt membrane (spectropore) to remove unincorporated [$^{35}$S]-methionine. A sample of labeled uncoupled virus was retained. 0.5M of $MgCl_2$ was added to the uncoupled sample to prevent aggregation.

Next, the virus was conjugated to PEG. The viral lot was collected and combined with a methoxypolyethylene glycol tresylate, mwt 5000 (Sigma M3938, 138H51681) at weight ratio of 40 mg tresyl PEG to 1 mg virus. (1 OD 260=$2 \times 10^{13}$ viral partials=185 mg protein per ml. Mwt. 120M daltons. [Virology Labfax, D. R. Harper(Ed). Bios Scientific. Oxford. 1998]). The reaction of coupling the protein to PEG was 3 hr. The reaction mixture was then dialyzed overnight in sterile 18,000 mwt dialysis membrane to allow removal of excess unreacted PEG. The final batch contained 9,400 CPM/ul for PEG modified virus and 1,786 CPM/ul for non-PEG virus. The difference is due to volume differences after dialysis. By adjusting doses to give equal [$^{35}$S]-methionine counts—very precise dosing could be achieved.

The coupling was analyzed by determining the partition coefficient in a biphasic system. Briefly, 18 g of a biphasic system of 4.75% (w/w) PEG8000 over 4.75% Dextran 70 in 0.15M NaCl, 0.01M $NaPO_4$ pH 6.80 was prepared. 10 ul of [$^{35}$S]-methionine labeled PEG/RIII or [$^{35}$S]-methionine labeled NonPEG/RIII were added in duplicate to 4 g tubes. The system was inverted 30 times and allowed to settle overnight. Partitioning (K) is the ratio of the top to bottom [$^{35}$S]-methionine counts. After partitioning this gave a ratio of top PEG counts to bottom Dextran counts of average K of 1.4(1147/756, 882/687). When the virus batch was coupled with 1:20 mg/mg tresyl PEG the average K was 13.2 (546/46,721/49 background subtracted 10 min counts). When the virus batch was coupled at a 1:40 ratio the K averaged 17 (952/61, 515/27, 20 min counts). Thus, as shown in FIG. 1, there was not much change between the 1:20 and the 1:40 ratio and the system appeared to be saturated at the 1:40 ratio. (Log K uncoupled=0.15, log 1:20 ratio=1.12, log 1:40 ratio=1.23).

For comparison PEG-BSA has a K of 10 when the 60 lysyl residues per BSA molecule are saturated with PEG. Thus, given the large molar excess of PEG in the reaction mixture, PEG saturation of RIII virus is likely to be complete.

Using a 1:40 ratio of PEG to virus excess resulted in predictable saturation of all potential lysyl coupling sites. It is envisioned that saturation yields a reproducible system. The toxicity of PEG/RIII is anticipated to be low and an increased dose is feasible. PEG-modification favors viral receptor driven interventions over antibody driven interactions by effectively "lowering" the apparent concentration of epitopes.

Non-denaturing SDS page gels 5% over 10% Laemilli buffers were used to further characterize the purity of the test lot preparation.

Example 4

Viability of a Modified Virus

To demonstrate preservation of viability of the virus, the titration of PEG virus was compared to the parent non-PEG viral lot. The PEG virus was diluted 1000 fold (to lower MgCl levels) and titered on primary rhesus monkey kidney. The titer for non-PEG was 10 fold higher than for the PEG virus at day five. However, by day 10 this difference had largely disappeared. At day 10 non-PEG virus had a titer of $1.8 \times 10^5$ vs. PEG virus titer of $1.1 \times 10^5$. Thus, the virus was not killed by the PEG coupling, but its speed to lysis was delayed. This may be explained by PEG interfering with adsorption of virus to receptor.

Furthermore, retention of receptor specificity was demonstrated by titering the virus on NIH3T3 (low permissive parent lacking the receptor) vs. D104 (Rat Her/2nu stably transformed NIH3T3, having Her/2nu as the receptor). The PEG virus was diluted and then titered on both cell types in serum free media. Serum was added at 24 hr. The PEG virus titers to $10^5$ on D104 but only to $10^3$ on the parental cell line. Thus, the PEG virus was alive, as demonstrated by equal titration levels on PRMK at day 10, and retained its ability to interact with surface receptors (Her/2nu, a member of the tyrosine kinase receptor family).

Example 5

Infectivity of a Modified Virus

The PEG modified RIII was compared to non-modified RIII for infectivity and infectivity in the presence of anti-reovirus III ascites.

Limiting dilution titers were determined as described above, but the starting virus inoculum was matched by normalizing to equal [$^{35}$S]-methionine counts. PRMK was used as the indicator cell line. Tubes with ascites had 20 ul filter sterilized mouse antiRIII ascites added per 1 ml of serum protein free Rh medium. In two experiments the presence of antibody affected the titer of non-PEG virus by two dilutions. 10 ul of non PEG viral inoculum titered to $10^{-5}$ in the absence of antibody but to only $10^{-3}$ in the presence of Ab. PEG/RIII titered to $10^{-4}$ in both the presence and absence of antibody. Thus, although PEG modification interfered with viral adsorption, it also negated the effect of antibody.

Example 6

In Vitro Treatment of Leukemia

To demonstrate that the modified reovirus system works in hematopoietic cells, a human acute myclo-monocytic leukemia cell line, U937 was used.

Briefly, the cells were established at sub-confluence in a medium. The U937 cells were inoculated with the modified PEG-reovirus at a high MOI. Viral growth was allowed to proceed to complete cell lysis, and cell debris was removed by centrifugation. Analysis was done by limiting dilution and by acridine orange staining for intracytoplasmic inclusions Lysis of this leukemia was apparently 100%, ($\sim 10^{10}$ cells were lysed with no resistant variants developing in vitro). Thus, this data suggest that some human leukemia cells are susceptible to the present invention.

Example 7

Administration of PEG/reovirus to Treat Leukemia

The U937 cells were also used in a Nude mouse leukemia model. Briefly, 3 nude mice that received $10^6$ U937 alone showed 50% circulating blasts at 7 days, while 3 mice that received $10^6$ U937 cells plus one injection at day 1 (24 hrs later) of $10^6$ PEG/Reovirus showed no or few blasts by Giemsa stain or by CD 13 monocytic lineage specific immunostain at day 12. Thus, this data suggested that the PEG/Reovirus was therapeutic for the treatment of some forms of leukemias. It is also contemplated that multiple doses can be given.

Example 8

Clearance of PEG Modified Virus Versus Non-PEG Modified Virus

PEG/RIII was compared to NonPEG/RIII in vivo to obtain data on the rate of clearance from the circulation.

Figure 2:
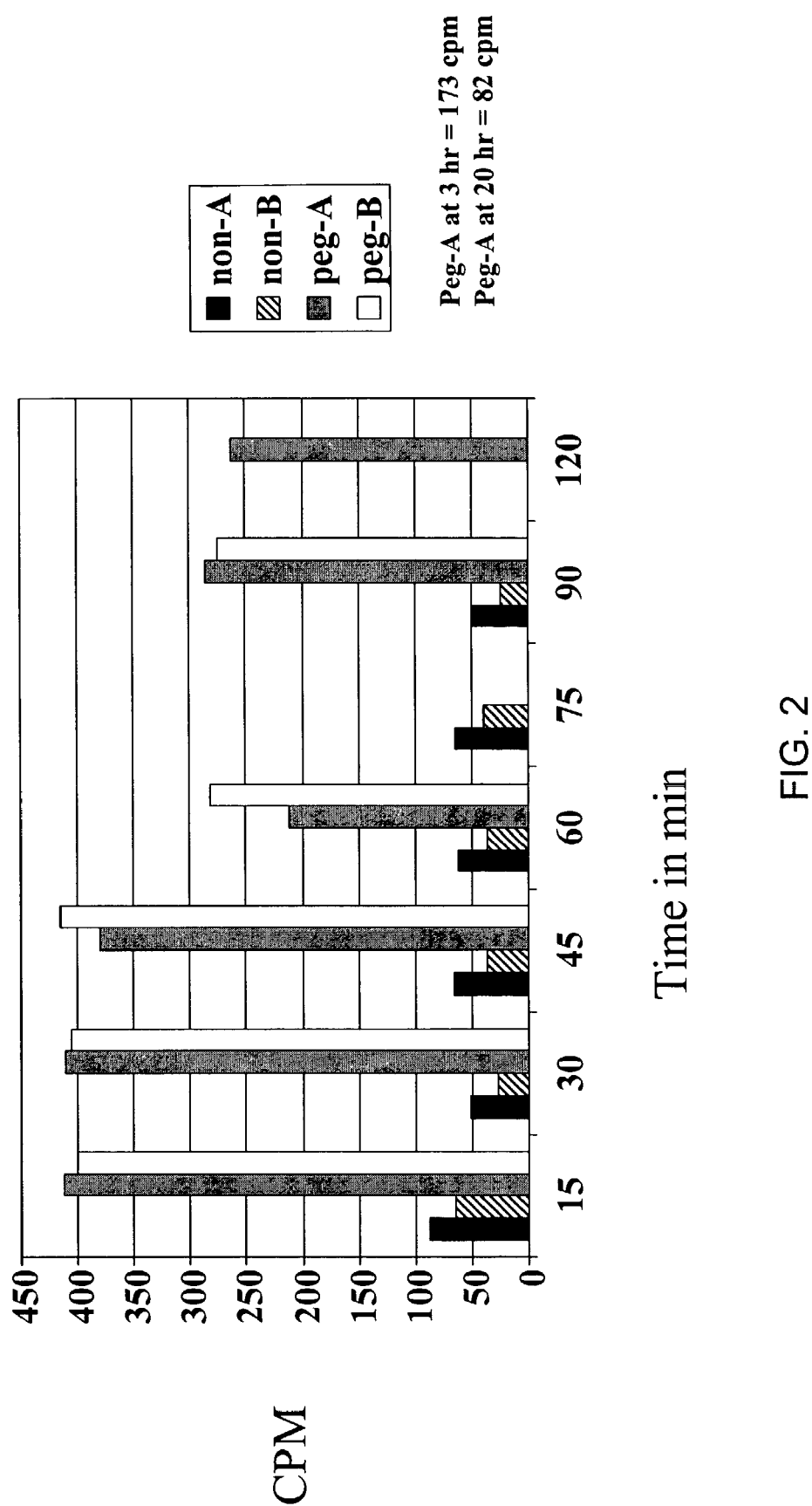
FIG. 2. This figure illustrates the clearance of a modified reovirus versus an unmodified reovirus following intravascular injection. The figure shows radioactive counts recovered from blood samples of Balb/C mice following injection of polyethylene glycol modified reovirus (PEG-A, PEG-B) compared to unmodified virus (non-A, and non-B).

Briefly, equal numbers of [$^{35}$S]-methionine counts corresponding to equal viral doses were given to four reovirus naive mice. Assuming a blood volume to weight ratio similar to humans, the maximum expected counts per 25 ul sample were approximately 1000. PEG/RIII quickly plateaued at 400 counts/ 25 ul whole blood sample with approximately 40% of counts remaining after 20 hrs. Non PEG/RIII immediately (at the first time point) decreased to 70 CPM and declined rapidly. This result indicated that PEG modification prolonged the circulatory survival of PEG/RIII (FIG. 2).

It was not surprising that naive mice rapidly cleared virus. There are many cell types with appropriate G protein receptors for reovirus, and additional non-specific clearance mechanisms. Thus, this PEG modification scheme preserved infectivity, blocked Ab interference, and prolonged clearance.

Example 9

Mouse Toxicity Studies

A mouse toxicity study was performed. Briefly, Balb/C mice that were certified to be reovirus sero-negative were obtained. 26 animals matched in weight (+/−3 g) were recaged for the experiment. The sero-negative status was confirmed. To confirm sero-negative status, L cells were infected with RIII. After 2 days, the infected Lcells were washed with fresh media, dispensed on slides, air-dried, methanol fixed, and frozen desiccated at −70° C. After warming, slides were blocked with 1% albumin 0.1% Tween 20 in PBS pH7.2 for 1 hr. For positive control slides, 2 ul per ml of mouse anti-reovirus ascites was added to blocking buffer and slides incubated for 1 hr at 35° C. Serum from test animals was diluted 1:4 with blocking buffer and incubated for 1 hr at 35° C. The slides were then washed in PBS and exposed to FITC labeled goat anti-mouse IgG (Chemicon 5024R), with 0.01 Evans blue for 1 hr at 35° C. After a final wash, slides were mounted with Chemicon low fluorescent mounting medium and examined. All 26 test animals were negative by this assay. Positive controls using anti RIII ascites were strongly positive.

For the toxicity studies, the 26 mice were then divided into 3 groups: A) nine animals received $2 \times 10^6$ RIII, B) eight received $2 \times 10^7$, and C) nine received $2 \times 10^8$. All animals were well-appearing 10 days later. All animals were sacrificed and samples were removed from lung, gut, kidney, brain and placed in 10% formaldehyde /PBS pH7.2. After 4 week, formaldehyde fixed tissues were paraffin embedded and sectioned. Tissue sections were de-paraffinized and immersed into 10% formaldehyde/PBS pH7.2 until staining.

An IFA method was used to analyze the samples. Briefly, RIII positive L cells and virus bearing tumor cells from tumor tissue (from efficacy pilot study below) were used as positive controls. Anti-RIII ascites was made by injecting heat/pH killed reovirus. (60° C. 1 hr at pH9) in complete fruends adjuvant on 4 or 5 occasions intraperitoneal, then at 5 months 1 ml pristine intraperitoneal, one week later $10^8$ Sp2/0 cells intraperitoneal, abundant "polyclonal ascites" was collected over 2 weeks. Anti RIII was diluted 1:10 in PBS 1% albumin, 0.05% Tween 20, and goat anti-mouse FITC (Chemicon) was used as provided. For staining, all slides were immersed in PBS to remove formaldehyde (15 min each), then immersed in 10% FBS in the above blocking buffer for 1 hr. Slides were washed in PBS and immersed in PBS 10% sucrose, 0.5% NP40. Slides were washed in 1% FBS PBS. Ascites diluted 1:10 in blocking buffer was applied as 40 ul drop and spread if necessary to cover tissue section. Slides were incubated 40 min at 35° C., washed with PBS, conjugate was added and incubated 40 min at 35° C., washed, and mounted.

Of 60 samples that were examined, 47 samples were from the above toxicity challenge groups and 13 were from 2 animals given Sp2/0 tumor and virus and sacrificed at 9 days as positive controls. Two of the remaining 47 specimens had positive cells identified. Animal 14 had few positive cells in kidney. Animal 2 few positive cells in lung. Animal 14 received $2\times10^7$ and animal 2 received $2\times10^6$ RIII. The two tumor barring animals both gave positive results in the tumor tissue but one was positive in one spot also in liver tissue. Other tissues from tumor bearing animals were negative but unfortunately brain from both animals was uninterpretable due to high background in both specimens. These animals were ill-appearing probably due to ascites, but no neurologic symptoms were noticed. Regarding the normal toxicity challenge animals, all appeared perfectly healthy even at the highest dose categories. Therefore, the 35 negative stains on the challenge animals suggested a low degree of toxicity associated with this virus even when the animals were challenged by intravenous injection.

TABLE 5

Summery of reovirus toxicity challenge

| | |
|---|---|
| Number of Animals negative by IFA 24 | (92.3%) |
| Number of Animals positive by IFA 2 | (7.7%) |
| Number of samples negative by IFA 38[a] | (95.0%) |
| Number of samples positive by IFA 2 | (5.0%) |

[a]Neg samples = 14/14 gut, 11/12 kidney, 7/7 brain, 6/7 lung

Example 10

SCID Mouse Toxicity Model

SCID mice are devoid of all T cell and B cell function, but it is envisioned that they the intrinsic ability through a double stranded RNA recognition protein to shut down reovirus replication.

To begin, a dose that results in no systemic illness by thirty days is given to the SCID mice. This dose has been shown in art for the reovirus 3 strain (Tyler and Oldstone, 1998), and it is envisioned that the PEG reovirus 3 is less toxic due to its more gradual adsorption to receptors.

Briefly, $2\times10^7$ rapidly growing leukemia cells (OL1-AML3, or U937) are given to female SCID(scid/scid) mice that are closely matched in weight. The tumor is allowed to establish for one day and then a range of doses of PEG reovirus 3 is given on day 1, 5 and 10. The data will demonstrate the dose range that clears or significantly reduces the AML in at least some fraction of the mice.

Example 11

Rhesus Toxicity Model

Although reoviruses are highly conserved, variation in Sigma-1 has been demonstrated. Indeed, σ-1 is the principle protein required for receptor interaction, and change in σ-1 correlates with most phenotypic changes including virulence, and the range of toxic effects seen in normal tissues. It is indeed fortuitous that PEG modification under saturating conditions did not destroy receptor interaction. As stated earlier σ-1 targets sialac acid on G protein like molecules, important examples include ErbB and Her2. Because RNA viruses are intrinsically more mutable and in reovirus these mutations usually tract to σ-1, it is critical to establish that the master lot viral that is produced is not associated with a mutation that confers unexpected toxicity.

Briefly, monkeys are administered two dose level intravenous challenges PEG reovirus 3, day 0 ($10^6$) and day 2 ($10^8$). Intra-cerebral challenges are also envisioned. Baseline and serial blood samples are analyzed by viral culture and DFA. On day 8, monkeys are sacrificed and necropsy is performed. A total of 3 animals are proposed, they are challenged with escalating doses of the modified master lot virus.

Example 12

Treatment Regimen for Leukemia

It is envisioned that leukemia may be treated by employing the Reoviridae virus composition of the present invention. For example, PEG/Reovirus may be employed at a starting dose of $5\times10^9$ pfu by infusion for a 70 kg patient with 100 leukemia blasts/mm$^3$ (approximately 1 virus to 1 leukemia cell). Dosing may be every 3 weeks for 4 cycles (total=12 weeks), at which time response may also be determined. If no dose-limiting toxicity is observed after 2 cycles, then the next dosing level may be initiated according to standard dose-escalation algorithms.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

REFERENCES

The following references, to the extent that they provide exemplary procedural or other details supplementary to those set forth herein, are specifically incorporated herein by reference.

U.S. Pat. No. 6,136,307
U.S. Pat. No. 6,110,461
U.S. Pat. No. 5,846,945
U.S. Pat. No. 5,830,880
U.S. Pat. No. 5,824,348
U.S. Pat. No. 5,824,311
U.S. Pat. No. 5,801,005
U.S. Pat. No. 5,798,339
U.S. Pat. No. 5,739,169
U.S. Pat. No. 5,641,515
U.S. Pat. No. 5,633,016
U.S. Pat. No. 5,543,158
U.S. Pat. No. 5,466,468
U.S. Pat. No. 5,399,363
Abuchowski A. et al., *Cancer Biochem. Biophys.* 7:175–186, 1984.
Abuchowski A. et al., *J. Biol. Chem.* 252:3582–3586, 1977.
Armstrong, G. D. et al. *Virology* 138:37, 1984.
Austin-Ward and Villaseca, *Rev. Med. Chil.,* 126:838–45, 1998.

Bajorin et al., *Proc. Annu. Meet. Am. Soc. Clin. Oncol.*, 7:A967, 1988.
Bakhshi et al., *Cell*, 41:899–906, 1985.
Beaupre D M. et al., *Cancer Research.* 59(12):2911–80, 1999.
Beaupre D M. et al., *Investigational New Drugs.* 17(2):137–43, 1999.
Beaupre D M. et al., *Journal of Clinical Oncology.* 17(3):1071–9, 1999.
Brizel, *Semin. Radiat. Oncol.*, 8(4 Suppl. 1):17–20, 1998.
Bukowski et al., *Clin. Cancer Res.*, 4(10):2337–47, 1998.
Christodoulides et al., *Microbiology*, 144(Pt 11):3027–37, 1998.
Cleary and Sklar, *Proc. Nat'l. Acad. Sci. USA*, 82:7439–43, 1985.
Cleary et al., *J. Exp. Med.*, 164:315–20, 1986.
Coffey M C. et al., *Science.* 282(5392): 1332–4, 1998.
Coffin, In: *Virology*, Fields et al. (eds.), New York: Raven Press, pp. 1437–1500, 1990.
Culver et al., *Science*, 256:1550–1552, 1992.
Curran, *Semin. Radiat. Oncol.*, 8(4 Suppl. 1):2–4,1998.
Davidson et al., *J. Immunother.*, 21:389–98, 1998.
Delgado C. et al., *Biotechnol. Appl. Biochem.* 12:119–128, 1990.
Derrien M. and Fields B N. *Virology.* 257(1):35–44, 1999.
Dillman, *Cancer Biother. Radiopharm.*, 14(1):5–10, 1999.
Duncan M R., et al., *Journal of Virology.* 28(2): 444–9, 1978.
el-Kareh, Secomb, *Crit. Rev. Biomed. Eng.*, 25:503–71, 1997.
Erlandsson, *Cancer Genet. Cytogenet*, 104:1–18, 1998.
Fields B. N. et al., In: *Fields Virology*, $3^{rd}$ *Edition*, Lippincott Williams & Wilkins 1553–1766, 1996.
Fields, B. N. et al., *Fundamental Virology*, 3rd Edition, Lippincott-Raven, 1996.
Francis G. E. et al., *Int. J. Heamtol* 68:1–18, 1998.
Gentsch, J. R. K. & Pacitti, A. F. *J. Virol.* 56:356, 1985.
Gertig and Hunter, *Semin. Cancer Biol.*, 8(4):285–298, 1997.
Hanibuchi et al., *Int. J. Cancer*, 78:480–5, 1998.
Hashiro G. et al., *Archives of Virology*, 54(4): 307–15, 1977.
Hsiung, G. D. in *Hsiung. Diagnostic Virology*, Yale university Press, New Haven and London, 1994.
Hellstrand et al., *Acta. Oncol.*, 37:347–53, 1998.
Hill C L., et al., *Nature Structural Biology* 6(6): 565–8, 1999.
Ho et al., *Cancer,* 83:1894–907, 1998.
Hollstein et al., *Science* 253:49–53, 1991.
Hui and Hashimoto, *Infect. Immun.*, 66:5329–36, 1998.
Irie et al., "Melanoma gangliosides and human monoclonal antibody," In: *Human Tumor Antigens and Specific Tumor Therapy*, Metzgar & Mitchell (eds.), Alan R. Liss, Inc., New York, pp. 115–126, 1989.
Irie & Morton, *Proc. Nat'l Acad. Sci. USA* 83:8694–8698, 1986.
Jackson G. G. & Muldoon R. L. *J. Infect. Dis.* 128:811, 1973.
Johnson and Hamdy, *Oncol. Rep.*, 5:553–557, 1998.
Kasel J A., et al., Infection of human volunteers with a reovirus of bovine origin. Reprinted from PROCEEDINGS OF THE SOCIETY FOR EXPERIMENTAL Biology and Medicine, 1963, 112, 979–981.
Kerr et al., *Br. J. Cancer,* 26:239–57, 1972.
Kolmel, *J. Neurooncol.*, 38:121–125, 1998.
Liebermann et al., *Int. J. Oncol.*, 12:685–700, 1998.
Magi-Galluzzi et al., *Anal. Quant. Cytol. Histol.*, 20:343–350, 1998.
Mangray and King, *Front Biosci.*, 3:D1148–1160, 1998.
Mayer, *Cancer Metastasis Rev.*, 17:211–8, 1998.
Mitchell et al., *Ann. N.Y. Acad. Sci.*, 690:153–166, 1993.
Mitchell et al., *J. Clin. Oncol,.* 8:856–859, 1990.
Morton D. L., and Ravindranath, M. H. Current concepts concerning melanoma vaccines. In *Tumor Immunology*, Dalgleish A G (ed.), London: Cambridge University Press, 1–55, 1996.
Morton et al., *Ann. Surg.* 216: 463–482, 1992.
Mougin et al., *Ann. Biol. Clin.* (Paris), 56:21–28, 1998.
Mumby and Walter, *Cell Regul.*, 2:589–598, 1991.
Murphy F. A. et al., Sixth Report of the International Committee on Taxonomy of Viruses. Vienn: springer-Verlag, 1997.
Natoli et al., *Biochem. Pharmacol.*, 56(8):915–920, 1998.
Neutra M R. *Journal of Infectious Diseases* 179 Suppl 3:S441–3, 1999.
Norman K L & Lee P W. *Journal of Clinical Investigation* 105(8): 1035–8, 2000.
Ochi et al., *Am. J. Gastroenterol.*, 93:1366–1368, 1998.
Ohara, *Gan. To. Kagaku. Ryoho.*, 25:823–8, 1998.
Paul R. W. et al. *Virology* 172:382–385, 1989.
Pietras et al., *Oncogene*, 17:2235–49, 1998.
Qin et al., *Proc. Nat'l Acad. Sci. USA,* 95(24):1411–6, 1998.
Ravindranath, M. H. and Morton, D. L. *Intern. Rev. Immunol.* 7: 303–329, 1991.
Remington's Pharmaceutical Sciences, 15th Edition, pages 1035–1038 and 1570–1580
Remington's Pharmaceutical Sciences, 18th Ed. Mack Printing Company, 1990, pp. 1289–1329
Rosen, L. *Am. J. Hyg.* 71:242, 1960.
Rosenberg et al., *N. Engl. J. Med.*, 319:1676, 1988.
Rovere et al., *J Leukoc Biol.* 66:345–9, 1999.
Sabin A. B. *Science* 130:1387–1389, 1959.
Serrano et al., *Nature*, 366:704–707, 1993.
Serrano et al., *Science*, 267:249–252, 1995.
Solyanik et al., *Cell Prolif.*, 28:263–278, 1995.
Stanley N. F. In: *Comparative Diagnosis of Viral Diseases*, 385–421, Academic Press, New York, 1974.
Stanley, N. F. *Br. Med. Bull.* 23:150, 1967.
Steinman et al., *Hum Immunol.* 60:562–7, 1999.
Stokke et al., *Cell Prolif,* 30(5):197–218, 1997.
Strong J E et al., *EMBO Journal* 17(12):3351–62, 1998.
Tyler and Oldstone. *Current topics in Microbiology.* 233: 147–161, 1998.
Thomis D C et al., *Journal of Virology* 12: 7695–700, 1993.
Tsujimoto and Croce, *Proc. Natl. Acad. Sci. USA*, 83:5214–8, 1986.
Tsujimoto et al., *Science*, 228:1440–3, 1985.
Weinberg, *Science*, 254:1138–1145, 1991.
Yue Z & Shatkin A J. *Virology* 234(2): 364–71, 1997.

What is claimed is:

1. A pharmaceutical composition comprising a Reoviridae virus conjugated to one or more carbohydrates dispersed in a pharmaceutically acceptable carrier.

2. The pharmaceutical composition of claim 1, wherein the Reoviridae virus is a reovirus.

3. The pharmaceutical composition of claim 2, wherein the reovirus is human serotype 3 reovirus.

4. The pharmaceutical composition of claim 1 further comprising a cell-targeting moiety conjugated with said virus within the pharmaceutical composition.

5. The pharmaceutical composition of claim 4, wherein the targeting moiety is an antibody.

6. The pharmaceutical composition of claim 5, wherein the antibody is C225, Trastuzuab, 1D5, PB3, TA-1, 4d5, Edrecolomab, CC49, Mc5, N901, CD56, MDX447, HMFG1, or IDEC-C2B8.

7. The pharmaceutical composition of claim 1, wherein the carbohydrate is mannose, galactose, dextran, cellulose, starch, glycogen, agarose, guar gum, pullulan, inulin, xanthan gum, carrageenin, pectin, or alginic acid hydrolysates.

8. The pharmaceutical composition of claim 1, wherein the carbohydrate is dextran.

* * * * *